US 8,741,333 B2

(12) United States Patent
Zhang et al.

(10) Patent No.: US 8,741,333 B2
(45) Date of Patent: *Jun. 3, 2014

(54) COMPOSITIONS AND METHODS FOR TREATING DERMATITIS OR PSORIASIS

(75) Inventors: Jie Zhang, Salt Lake City, UT (US); Kevin S. Warner, West Jordan, UT (US); Sanjay Sharma, Sandy, UT (US)

(73) Assignee: Nuvo Research Inc., Mississauga, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/640,140

(22) Filed: Dec. 14, 2006

(65) Prior Publication Data

US 2007/0196459 A1    Aug. 23, 2007

Related U.S. Application Data

(63) Continuation-in-part of application No. 11/146,917, filed on Jun. 6, 2005.

(60) Provisional application No. 60/750,637, filed on Dec. 14, 2005, provisional application No. 60/750,524, filed on Dec. 14, 2005, provisional application No. 60/577,536, filed on Jun. 7, 2004.

(51) Int. Cl.
*A61F 13/00* (2006.01)
*A61K 9/00* (2006.01)
*A61K 9/70* (2006.01)
*A61L 26/00* (2006.01)

(52) U.S. Cl.
CPC ............. *A61K 9/0014* (2013.01); *A61K 9/7015* (2013.01); *A61L 26/0076* (2013.01)
USPC ....................................................... 424/443

(58) Field of Classification Search
None
See application file for complete search history.

(56) References Cited

U.S. PATENT DOCUMENTS

| | | | |
|---|---|---|---|
| 4,430,325 A | 2/1984 | Gaffar et al. | |
| 4,645,502 A | 2/1987 | Gale et al. | |
| 4,695,465 A | 9/1987 | Kigasawa et al. | |
| 4,780,320 A | 10/1988 | Baker | |
| 4,956,171 A | 9/1990 | Chang | |
| 5,091,171 A | 2/1992 | Yu et al. | |
| 5,183,459 A | 2/1993 | Bernard | |
| 5,370,879 A | 12/1994 | Masterson et al. | |
| 5,378,730 A | 1/1995 | Lee et al. | |
| 5,399,355 A | 3/1995 | Riedl et al. | |
| 5,460,820 A | 10/1995 | Ebert et al. | |
| 5,589,156 A | 12/1996 | Henry | |
| 5,658,583 A | 8/1997 | Zhang et al. | |
| 5,707,981 A * | 1/1998 | Chriki | 514/170 |
| 5,733,572 A | 3/1998 | Unger et al. | |
| 5,741,510 A | 4/1998 | Rolf et al. | |
| 5,747,022 A | 5/1998 | Slavtcheff | |
| 5,747,060 A | 5/1998 | Sackler et al. | |
| 5,885,597 A | 3/1999 | Botknecht et al. | |
| 5,906,814 A | 5/1999 | Epstein | |
| 5,955,502 A | 9/1999 | Hansen et al. | |
| 6,036,966 A | 3/2000 | Youssefyeh | |
| 6,045,814 A | 4/2000 | Roulier et al. | |
| 6,143,794 A | 11/2000 | Chaudhuri et al. | |
| 6,207,184 B1 | 3/2001 | Ikeda et al. | |
| 6,207,703 B1 | 3/2001 | Ponikau | |
| 6,211,250 B1 | 4/2001 | Tomlinson et al. | |
| 6,221,915 B1 | 4/2001 | McCleane | |
| 6,245,347 B1 | 6/2001 | Zhang et al. | |
| 6,290,984 B1 | 9/2001 | Tapolsky et al. | |
| 6,290,986 B1 | 9/2001 | Murdock et al. | |
| 6,324,424 B1 | 11/2001 | Ledger et al. | |
| 6,342,537 B1 | 1/2002 | Thomsen et al. | |
| 6,387,383 B1 | 5/2002 | Dow et al. | |
| 6,391,869 B1 | 5/2002 | Parks et al. | |
| 6,395,955 B1 | 5/2002 | Roe et al. | |
| 6,432,415 B1 * | 8/2002 | Osborne et al. | 424/400 |
| 6,455,066 B1 | 9/2002 | Fischer et al. | |
| 6,495,124 B1 | 12/2002 | Samour | |
| 6,528,086 B2 * | 3/2003 | Zhang | 424/449 |
| 6,562,363 B1 * | 5/2003 | Mantelle et al. | 424/434 |

(Continued)

FOREIGN PATENT DOCUMENTS

CN    1426815    7/2003
CN    1739487    3/2006

(Continued)

OTHER PUBLICATIONS

Cameo Chemicals Chemical Data Sheet (2 pages) obtained from http://cameochemicals.noaa.gov/chemical/565.*
Nortier, Y.L.M. et al. "Preparation and stability testing of a hydrogel for topical analgesia," Jul. 1995, pp. 214-217.
An, Na-Mi et al. "Development of a Novel Soft Hydrogel for the Transdermal Delivery of Testosterone," Drug Development and Industrial Pharmacy, 2003, pp. 99-105, vol. 29, No. 1.
Padilla et al., Topical Medications for Orofacial Neuropathic Pain: A Review, J Am Dent Assoc, vol. 131, No. 2, (2000), pp. 184-195, p. 185-p. 191.
Farber et al., Serotonergic Agents That Activate 5HT2A Receptors Prevent NMDA Antagonist Neurotoxicity, Neuropsychopharmacology, 1998, vol. 18, No. 1, pp. 57-62, p. 60.

(Continued)

*Primary Examiner* — Brian Gulledge
(74) *Attorney, Agent, or Firm* — Thorpe North & Western LLP

(57) ABSTRACT

The present invention is drawn to adhesive solidifying formulations for treating skin disorders, such as dermatitis or psoriasis. The formulation can include a drug, a solvent vehicle, and a solidifying agent. The solvent vehicle can include a volatile solvent system including at least one volatile solvent, and a non-volatile solvent system including at least one non-volatile solvent, wherein the non-volatile solvent system is capable of facilitating the delivery of the drug at therapeutically effective rates over a sustained period of time. The formulation can have a viscosity suitable for application to a skin surface prior to evaporation of the volatile solvents system. When applied to the skin, the formulation can form a solidified layer after at least a portion of the volatile solvent system is evaporated.

93 Claims, No Drawings

(56) References Cited

U.S. PATENT DOCUMENTS

| | | |
|---|---|---|
| 6,635,674 B1 | 10/2003 | Kaneko et al. |
| 6,653,346 B1 | 11/2003 | Wang et al. |
| 6,673,363 B2 | 1/2004 | Luo et al. |
| 6,962,691 B1 | 11/2005 | Lulla et al. |
| 7,223,418 B2 | 5/2007 | Hidaka et al. |
| 2002/0077328 A1 | 6/2002 | Hassan et al. |
| 2002/0111377 A1 | 8/2002 | Stinchcomb |
| 2002/0155140 A1 | 10/2002 | Sirinyan et al. |
| 2003/0018085 A1 | 1/2003 | Raoof et al. |
| 2003/0059471 A1 | 3/2003 | Compton et al. |
| 2003/0091519 A1 | 5/2003 | Zatz et al. |
| 2003/0096012 A1 | 5/2003 | Besse et al. |
| 2003/0118655 A1 | 6/2003 | Kundel |
| 2003/0185915 A1* | 10/2003 | Carlo et al. ............. 424/744 |
| 2004/0018241 A1 | 1/2004 | Houze et al. |
| 2004/0057985 A1 | 3/2004 | Bracht |
| 2004/0091534 A1 | 5/2004 | Geoghegan et al. |
| 2004/0143026 A1 | 7/2004 | Shah |
| 2005/0089539 A1 | 4/2005 | Scholz et al. |
| 2005/0158274 A1 | 7/2005 | Hunter et al. |
| 2005/0276842 A1 | 12/2005 | Zhang et al. |
| 2007/0189977 A1 | 8/2007 | Zhang et al. |
| 2007/0189978 A1 | 8/2007 | Zhang et al. |
| 2007/0189980 A1 | 8/2007 | Zhang et al. |
| 2007/0190124 A1 | 8/2007 | Zhang et al. |
| 2007/0196293 A1 | 8/2007 | Zhang et al. |
| 2007/0196323 A1 | 8/2007 | Zhang et al. |
| 2007/0196325 A1 | 8/2007 | Zhang et al. |
| 2007/0196452 A1 | 8/2007 | Zhang et al. |
| 2007/0196453 A1 | 8/2007 | Zhang et al. |
| 2007/0196457 A1 | 8/2007 | Zhang et al. |
| 2007/0196458 A1 | 8/2007 | Zhang et al. |
| 2007/0280972 A1 | 12/2007 | Zhang et al. |
| 2008/0019927 A1 | 1/2008 | Zhang et al. |

FOREIGN PATENT DOCUMENTS

| | | |
|---|---|---|
| EP | 0 002 426 | 6/1979 |
| EP | 0 386 960 | 9/1990 |
| EP | 0 455 396 | 11/1991 |
| GB | 2 004 746 | 4/1979 |
| JP | 01-110620 | 10/1987 |
| JP | 01-110623 | 4/1989 |
| JP | 110620 | 4/1989 |
| JP | 1110623 | 4/1989 |
| JP | 2279623 | 11/1990 |
| JP | 200086440 | 3/2000 |
| JP | 2002226354 | 8/2002 |
| WO | WO 92/13529 | 8/1992 |
| WO | WO 97/29735 | 8/1997 |
| WO | WO 97/38675 | 10/1997 |
| WO | WO 99/22717 | 5/1999 |
| WO | WO 99/49835 | 10/1999 |
| WO | 0122907 | 4/2001 |
| WO | WO 01/37890 | 5/2001 |
| WO | WO 01/43722 A2 | 6/2001 |
| WO | 0160325 | 8/2001 |
| WO | WO 02/055023 | 7/2002 |
| WO | WO 03/059390 | 7/2003 |
| WO | WO 03/105821 | 12/2003 |
| WO | 2006097474 | 9/2006 |
| WO | 2007070643 | 6/2007 |
| WO | 2007070679 | 6/2007 |
| WO | 2007070695 | 6/2007 |

OTHER PUBLICATIONS

Khazaeinia et al., "A comparison of gastrointestinal permeability induced by diclofenac phospholipid complex with diclofenac acid and its solium salt" J. Pharmacy and Pharmaceutical Science: 6(3): 352-359, 2003.

Handbook of Pharmaceutical Excipients (1988) p. 123 (Glycerin) and p. 241 (Propylene Glycol).

Testosterone, Vitamin D May Improve Aromatase Inhibitor Joint Problems; http://www.medconnect.com.sg/tabid/92/ctl/c35097/Testosterone-Vitamin-D-May-Improve-Aromatase-Inhibitor-Joint-Problems/Default.aspx; Jan. 13, 2010; 2 pages.

Panchagnula; "Feasibility studies of dermal delivery of paclitaxel with binary combination of ethanol and isopropyl myristate: roll of solubility, partitioning and lipid bilayer perturbation"; Farmaco, vol. 60, No. 11-12, Aug. 26, 2005 pp. 894-899.

Kondo; "Enhancement of transdermal delivery by superfluous thermodynamic potential. I. Thermodynamic analysis of nifedipine transport across the lipoidal barrier"; J. Pharmacobiodyn, vol. 10, Apr. 17, 1987, pp. 587-594.

Scary Nails?; www.loceryl.com.au; accessed Jun. 7, 2013 (sent by associate Apr. 19, 2013).

Wang, et al.; Expert Opinion, Pharmacother, 2001, 2(12); pp. 2051-2063.

Mackowiak; Clinical Infectious Diseases (2000) vol. 31 (Suppl. 5): p. S154-6.

R.D. Wang et al., "Update on ropivacaine" Expert Opin. Pharmacother., 2001, 2(12), pp. 2051-2063.

Dockrell et al., "Imiquimod and resiquimod as novel immunomodulators" J. Antimicrobial Chemother., 2001, 48, pp. 751-755.

Anonymous, Dermatological and Transdermal Formulations, Chapter 6, 2002 by Marcel Dekker, Inc., pp. 282-284, (case annex, Chapter 6, Formulation Strategies for Modulating Skin Permeation, Davis et al.).

MacKowiak, Brief History of Antipyretic Therapy, Clinical Infectious Diseases, 2000, 31 (Suppl 5), pp. S154-S156.

\* cited by examiner

COMPOSITIONS AND METHODS FOR TREATING DERMATITIS OR PSORIASIS

This application claims the benefit of U.S. Provisional Application Nos. 60/750,637 and 60/750,524, each of which was filed on Dec. 14, 2005, and is a continuation-in-part of U.S. application Ser. No. 11/146,917 filed on Jun. 6, 2005, which claims the benefit of U.S. Provisional Application No. 60/577,536 filed on Jun. 7, 2004, each of which is incorporated herein by reference.

FIELD OF THE INVENTION

The present invention relates generally to systems for treating skin disorders, such as dermatitis or psoriasis. More particularly, the present invention relates to adhesive solidifying formulations having a viscosity suitable for application to affected skin areas, and which forms a solidified layer that delivers drug.

BACKGROUND OF THE INVENTION

Skin disorders are common afflictions for many people. Some of the most common are dermatitis (also known as eczema) and psoriasis. Dermatitis or eczema are synonymous terms used to define an inflammatory skin reaction characterized histologically by spongiosis with varying degrees of acanthosis, and a superficial perivascular lymphohistiocytic infiltrate. It is a common skin condition affecting significant populations in industrial countries. It is particularly prevalent on the hands of workers in service industry because of the workers frequent contact with wet or irritating chemicals. It is also hereditary in many instances. Psoriasis is a common auto-immune skin disease. Both dermatitis and psoriasis can cause serious physical and/or psychological suffering to the subject regardless of the location on the body that these conditions occur, but they are particularly bothersome if they occur on the skin of the hand. Those afflicted with such disorders often have to use their hands in their work which can aggravate the condition.

Various therapies are available to treat dermatitis or psoriasis. Preventive measures including avoiding wet work and wearing recommended gloves, followed by topical treatment as the first line of therapy for acute and sub-acute cases. Several classes of topical drugs are available and are most frequently found in the form of creams, gels, or ointments. These drugs include corticosteroids such as betamethasone dipropionate, clobetasol propionate, halobetasol propionate, diflorasone diacetate, amcinonide, desoximethasone, fluocinonide, halcinonide, mometasone furoate, betamethasone valerate, fluocinonide, fluticasone propionate, triamcinolone acetonide, fluocinolone acetonide, flurandrenolide, desonide, hydrocortisone butyrate, hydrocortisone valerate, alclometasone dipropionate, flumethasone pivolate, hydrocortisone, and hydrocortisone acetate; immune system modulators such as tacrolimus and picrolimus; vitamin D3 and its analogs such as cholecalciferol, calcitriol, calcipotriol, and tacalcitol; and retinoic acids or their derivatives such as tazarotene. Persistent cases are often treated with oral corticosteroids such as prednisone, while chronic recalcitrant cases that cannot be controlled by topical or systemic corticosteroids are treated with light therapy in the form of PUVA carried out by ingestion of 8-methoxyproralen or by UV-B treatment.

Unfortunately, current therapies have many drawbacks. Oral medications frequently have undesirable side effects. Topically applied ointments and gel medications can be unintentionally removed from the treatment area when the skin is contacted by other objects. In addition, topically applied medications may spread onto surrounding healthy skin areas and cause undesirable adverse side effects including atrophy of healthy skin by exposure to corticosteroids, compromised immune system due to unnecessary contact by immune modulator drugs to large healthy skin areas, and irritation of healthy skin areas by retinoic acids or their derivatives. Dermal (including transdermal) patch dosage forms also are available in a few different forms, including matrix patch configurations and liquid reservoir patch configurations. In a matrix patch, the active drug is mixed in an adhesive that is coated on a backing film. Dermal (including transdermal) patch dosage forms also are available in a few different forms, including matrix patch configurations and liquid reservoir patch configurations. In a matrix patch, the active drug is mixed in an adhesive that is coated on a backing film. The drug-laced adhesive layer is typically directly applied onto the skin and serves both as means for affixing the patch to the skin and as a reservoir or vehicle for facilitating delivery of the drug. Conversely, in a liquid reservoir patch, the drug is typically incorporated into a solvent system which is held by a thin bag, which can be a thin flexible container. The thin bag can include a permeable or semi-permeable membrane surface that is coated with an adhesive for affixing the membrane to the skin. A shortcoming of dermal (including transdermal) patches is that they are usually neither stretchable nor flexible, as the backing film (in matrix patches) and the thin fluid bag (in reservoir patches) are typically made of polyethylene or polyester, both of which are relatively non-stretchable materials. If the patch is applied to a skin area that is significantly stretched during body movements, such as a joint, separation between the patch and skin may occur thereby compromising the delivery of the drug. In addition, a patch present on a skin surface may hinder the expansion of the skin during body movements and cause discomfort. Therefore, it would be desirable to have a topical formulation that is easy to apply, stays on the diseased skin area, and delivers the active drug continuously. It would also be desirable to have a formulation that is resistant to removal from the treatment site and can be confined spreading onto skin outside the intended to treatment area.

SUMMARY OF THE INVENTION

It has been recognized that it would be advantageous to provide dermal solidifying formulations that can be used for treating dermatitis or psoriasis, methods of treating dermatitis or psoriasis, and solidified layers for treating such skin disorders. In accordance with this, an adhesive solidifying formulation for treating dermatitis or psoriasis can comprise a drug suitable for treating dermatitis or psoriasis, a solvent vehicle, and a solidifying agent. The solvent vehicle can include a volatile solvent system including one or more volatile solvents, and a non-volatile solvent system including one or more non-volatile solvents. The non-volatile solvent system can be capable of facilitating the delivery of the drug into the tissues to be treated at a therapeutically effective rate over a sustained period of time. The formulation can have a viscosity which is suitable for application and adhesion to a skin surface prior to evaporation of the volatile solvent system. Upon application to the skin surface as a layer, the formulation can form a solidified layer after at least partial evaporation of the volatile solvent system, and can continue to deliver drug after the volatile solvent system is at least substantially evaporated.

In an alternative embodiment, a method of dermally delivering a drug topically for treating dermatitis or psoriasis can include applying an adhesive solidifying formulation to a skin surface of a human suffering from dermatitis or psoriasis (such as hand dermatitis). The adhesive solidifying formulation can comprise a drug effective for treating dermatitis or psoriasis, a solvent vehicle, and a solidifying agent. The solvent vehicle can comprise a volatile solvent system including at least one volatile solvent, and a non-volatile solvent system including at least one non-volatile solvent, wherein the non-volatile solvent system is preferably capable of facilitating delivery of the drug at therapeutically effective rates over a sustained period of time. The formulation can have a viscosity suitable for application and adhesion to the skin surface as a layer prior to evaporation of the volatile solvent system. Additional steps include solidifying the formulation to form a solidified layer on the skin surface by at least partial evaporation of the volatile solvent system; and dermally delivering the drug from the solidified layer to or across the skin at therapeutically effective rates for treating the dermatitis or psoriasis over a sustained period of time.

In another embodiment, a solidified layer for delivering a drug for treating dermatitis or psoriasis can comprise a drug effective for treating dermatitis or psoriasis; a non-volatile solvent system including at least one non-volatile solvent, wherein the non-volatile solvent system is capable of facilitating the delivery of the drug at therapeutically effective rates over a sustained period of time; and a solidifying agent. The solidified layer can have such degree of flexibility, cohesion, elasticity, and adhesion to skin, that it does not substantially separate from the skin surface to which the layer is applied for substantially the entire duration of the intended application time.

In another embodiment, a formulation for treating dermatitis or psoriasis (such as hand dermatitis) can comprise a drug, a solvent vehicle, and a solidifying agent. The drug can include at least one member selected from the group consisting of clobetasol propionate, clobetasol, derivatives thereof, or combinations thereof. The volatile solvent system can include at least one volatile solvent, and a non-volatile solvent system including propylene glycol and/or glycerol, and another non-volatile solvent including isostearic acid and/or oleic acid. The solidifying agent can include at least one member selected from the group consisting of polyvinyl alcohol, fish gelatin, zein, or combinations thereof. The formulation can have a viscosity suitable for application and adhesion to a skin surface prior to evaporation of the volatile solvent system. The formulation applied to the skin surface can form a solidified, coherent, flexible, and continuous layer after at least partial evaporation of the volatile solvent system. Additionally, the drug can continue to be delivered at the therapeutically effective rate after the volatile solvent system is at least substantially all evaporated.

Additional features and advantages of the invention will be apparent from the following detailed description which illustrates, by way of example, features of the invention.

DETAILED DESCRIPTION OF THE PREFERRED EMBODIMENT(S)

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a drug" includes reference to one or more of such compositions.

"Skin" is defined to include human skin (intact, diseased, ulcerous, or broken), finger and toe nail surfaces, and mucosal surfaces that are usually at least partially exposed to air such as lips, genital and anal mucosa, and nasal and oral mucosa.

The phrases "diseased skin" as it relates to a treatment area is defined as the skin region which is afflicted with a skin disorder, namely dermatitis or psoriasis.

The term "drug(s)" refers to any bioactive agent that is effective in treating a skin disorder, namely dermatitis (eczema) or psoriasis. More specifically, they include agents selected from the drug classes of corticosteroids, immune modulators, vitamin D3 and its analogs, retinoic acids and their pharmaceutically active derivatives, or combinations thereof. Specific non-limiting examples of drugs include betamethasone dipropionate, clobetasol propionate, halobetasol propionate, diflorasone diacetate, amcinonide, desoximethasone, fluocinonide, halcinonide, mometasone furoate, betamethasone valerate, fluocinonide, fluticasone propionate, triamcinolone acetonide, fluocinolone acetonide, flurandrenolide, desonide, hydrocortisone butyrate, hydrocortisone valerate, alclometasone dipropionate, flumethasone pivolate, hydrocortisone, hydrocortisone acetate, tacrolimus, picrolimus, tazarotene, isotretinoin, cyclosporin, anthralin, vitamin D3, cholecalciferol, calcitriol, calcipotriol, tacalcitol, calcipotriene, or combinations thereof. When referring generally to a "drug," it is understood that there are various forms of a given drug, and those various forms are expressly included. In accordance with this, various drug forms include polymorphs, salts, hydrates, solvates, and cocrystals. For some drugs, one physical form of a drug may possess better physical-chemical properties making it more amenable for getting to, into, or through the skin, and this particular form is defined as the "physical form favorable for dermal delivery." For example the steady state flux of diclofenac sodium from flux enabling non-volatile solvents is much higher than the steady state flux of diclofenac acid from the same flux enabling non-volatile solvents. It is therefore desirable to evaluate the flux of the physical forms of a drug from non-volatile solvents to select a desirable physical form/non-volatile solvent combination.

The phrases "dermal drug delivery" or "dermal delivery of drug(s)" shall include both transdermal and topical drug delivery, and includes the delivery of drug(s) to, through, or into the skin. "Transdermal delivery" of drug can be targeted to skin tissues just under the skin, regional tissues or organs under the skin, systemic circulation, and/or the central nervous system.

The term "flux" such as in the context of "dermal flux" or "transdermal flux," respectively, refers to the quantity of the drug permeated into or across skin per unit area per unit time. A typical unit of flux is microgram per square centimeter per hour. One way to measure flux is to place the formulation on a known skin area of a human volunteer and measure how much drug can permeate into or across skin within certain time constraints. Various methods (in vivo methods) might be used for the measurements as well. The method described in Example 1 or other similar method (in vitro methods) can also be used to measure flux. Although an in vitro method uses human epidermal membrane obtained from a cadaver, or freshly separated skin tissue from hairless mice rather than measure drug flux across the skin using human volunteers, it is generally accepted by those skilled in the art that results from a properly designed and executed in vitro test can be used to estimate or predict the results of an in vivo test with reasonable reliability. Therefore, "flux" values referenced herein can mean that measured by either in vivo or in vitro methods.

The term "flux-enabling" with respect to the non-volatile solvent system (or solidified layer including the same) refers to a non-volatile solvent system (including one or more non-volatile solvents) selected or formulated specifically to be able to provide therapeutically effective flux for a particular drug(s). For topically or regionally delivered drugs, a flux enabling non-volatile solvent system is defined as a non-volatile solvent system which, alone without the help of any other ingredients, is capable of delivering therapeutic sufficient levels of the drug across, onto or into the subject's skin when the non-volatile solvent system is saturated with the drug. For systemically targeted drugs, a flux enabling non-volatile solvent system is a non-volatile solvent system that can provide therapeutically effective daily doses over 24 hours when the non-volatile solvent system is saturated with the drug and is in full contact with the subject's skin with no more than 500 $cm^2$ contact area. Preferably, the contact area for the non-volatile solvent system is no more than 100 $cm^2$. Testing using this saturated drug-in-solvent state can be used to measure the maximum flux-generating ability of a non-volatile solvent system. To determine flux, the drug solvent mixture needs to be kept on the skin for a clinically sufficient amount of time. In reality, it may be difficult to keep a liquid solvent on the skin of a human volunteer for an extended period of time. Therefore, an alternative method to determine whether a solvent system is "flux-enabling" is to measure the in vitro drug permeation across the hairless mouse skin or human cadaver skin using the apparatus and method described in Example 1. This and similar methods are commonly used by those skilled in the art to evaluate permeability and feasibility of formulations. Alternatively, whether a non-volatile solvent system is flux-enabling can be tested on the skin of a live human subject with means to maintain the non-volatile solvent system with saturated drug on the skin, and such means may not be practical for a product. For example, the non-volatile solvent system with saturated drug can be soaked into an absorbent fabric material which is then applied on the skin and covered with a protective membrane. Such a system is not practical as a pharmaceutical product, but is appropriate for testing whether a non-volatile solvent system has the intrinsic ability to provide sufficient drug flux, or whether it is flux-enabling.

It is also noted that once the formulation forms a solidified layer, the solidified layer can also be "flux enabling" for the drug while some of the non-volatile solvents remain in the solidified layer, even after the volatile solvents (including water) have been substantially evaporated.

The phrase "effective amount," "therapeutically effective amount," "therapeutically effective rate(s)," or the like, as it relates to a drug, refers to sufficient amounts or delivery rates of a drug which achieves any appreciable level of therapeutic results in treating a condition for which the drug is being delivered. It is understood that "appreciable level of therapeutic results" may or may not meet any government agencies' efficacy standards for approving the commercialization of a product. It is understood that various biological factors may affect the ability of a substance to perform its intended task. Therefore, an "effective amount," "therapeutically effective amount," or "therapeutically effective rate(s)" may be dependent in some instances on such biological factors to some degree. However, for each drug, there is usually a consensus among those skilled in the art on the range of doses or fluxes that are sufficient in most subjects. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

"Therapeutically effective flux" is defined as the permeation flux of the selected drug that delivers sufficient amount of drug into or across the skin to be clinically beneficial in that some of the patient population can obtain some degree of benefit from the drug flux. It does not necessarily mean that most of the patient population can obtain some degree of benefit or the benefit is high enough to be deemed "effective" by relevant government agencies or the medical profession. More specifically, for drugs that target skin or regional tissues or organs close to the skin surface (such as joints, certain muscles, or tissues/organs that are at least partially within 5 cm of the skin surface), "therapeutically effective flux" refers to the drug flux that can deliver a sufficient amount of the drug into the target tissues within a clinically reasonable amount of time. For drugs that target the systemic circulation, "therapeutically effective flux" refers to drug flux that, via clinically reasonable skin contact area, can deliver sufficient amounts of the selected drug to generate clinically beneficial plasma or blood drug concentrations within a clinically reasonable time. Clinically reasonable skin contact area is defined as a size of skin application area that most subjects would accept. Typically, a skin contact area of 400 $cm^2$ or less is considered reasonable. Therefore, in order to deliver 4000 mcg of a drug to the systemic circulation via a 400 $cm^2$ skin contact area over 10 hours, the flux needs to be at least 4000 mcg/400 $cm^2$/10 hour, which equals 1 $mcg/cm^2/hr$. By this definition, different drugs have different "therapeutically effective flux. A therapeutically effective flux may be different in different subjects and or at different times for even the same subject. However, for each drug, there is usually a consensus among the skilled in the art on the range of doses or fluxes that are sufficient in most subjects at most times.

The term "plasticizing" in relation to flux-enabling non-volatile solvent(s) is defined as a flux-enabling non-volatile solvent that acts as a plasticizer for the solidifying agent. A "plasticizer" is an agent which is capable of increasing the percentage elongation of the formulation after the volatile solvent system has at least substantially evaporated. Plasticizers also have the capability to reduce the brittleness of solidified formulation by making it more flexible and/or elastic. For example, propylene glycol is a "flux-enabling, plasticizing non-volatile solvent" for the drug ketoprofen with polyvinyl alcohol as the selected solidifying agent. However, propylene glycol in a formulation of ketoprofen with Gantrez S-97 or Avalure UR 405 as solidifying agents does not provide the same plasticizing effect. The combination of propylene glycol and Gantrez S-97 or Avalure UR 405 is less compatible and results in less desirable formulation for topical applications. Therefore, whether a given non-volatile solvent is "plasticizing" depends on which solidifying agent(s) is selected.

It should be noted that "flux-enabling non-volatile solvent," "flux-enabling, plasticizing non-volatile solvent," or "high flux-enabling non-volatile solvent" can be a single chemical substance or a mixture of two or more chemical substances. For example, the steady state flux value for clobetasol propionate in is a 9:1 for propylene glycol:isostearic acid mixture that generated much higher clobetasol flux than propylene glycol or ISA alone. Therefore, the 9:1 propylene glycol:isostearic acid mixture is a "high flux-enabling non-volatile solvent" but propylene glycol or isostearic acid alone is not.

The term "adhesion" or "adhesive" when referring to a solidified layer herein refers to sufficient adhesion between the solidified layer and the skin so that the layer does not fall off the skin during intended use on most subjects. Thus, "adhesive" or the like when used to describe the solidified layer means the solidified layer is adhesive to the body surface to which the initial formulation layer was originally applied (before the evaporation of the volatile solvent(s)). In one embodiment, it does not mean the solidified layer is adhesive on the opposing side. In addition, it should be noted that whether a solidified layer can adhere to a skin surface for the desired extended period of time partially depends on the condition of the body surface. For example, excessively sweating or oily skin, or oily substances on the skin surface may make the solidified layer less adhesive to the skin. Therefore, the adhesive solidified layer of the current invention may not be able to maintain perfect contact with the body surface and deliver the drug over a sustained period of time for every subject under any conditions on the body surface. A standard is that it maintains good contact with most of the body surface, e.g. 70% of the total area, over the specified period of time for most subjects under normal conditions of the body surface and external environment.

The terms "flexible," "elastic," "elasticity," or the like, as used herein refer to sufficient elasticity of the solidified layer so that it is not broken if it is stretched in at least one direction by up to about 5%, and often to about 10% or even greater. For example, a solidified layer that exhibits acceptably elasticity and adhesion to skin can be attached to human skin over a flexible skin location, e.g., elbow, finger, wrist, neck, lower back, lips, knee, etc., and will remain substantially intact on the skin upon stretching of the skin. It should be noted that the solidified layers of the present invention do not necessarily have to have any elasticity in some embodiments.

The term "peelable," when used to describe the solidified layer, means the solidified layer can be lifted from the skin surface in one large piece or several large pieces, as opposed to many small pieces or crumbs.

The term "sustained" relates to therapeutically effective rates of dermal drug delivery for a continuous period of time of at least 30 minutes, and in some embodiments, periods of time of at least about 2 hours, 4 hours, 8 hours, 12 hours, 24 hours, or longer.

The use of the term "substantially" when referring to the evaporation of the volatile solvents means that a majority of the volatile solvents which were included in the initial formulation have evaporated. Similarly, when a solidified layer is said to be "substantially devoid" of volatile solvents, including water, the solidified layer has less than 10 wt %, and preferably less than 5 wt %, of the volatile solvents in the solidified layer as a whole.

"Volatile solvent system" can be a single solvent or a mixture of solvents that are volatile, including water and solvents that are more volatile than water. Non-limiting examples of volatile solvents that can be used in the present invention include denatured alcohol, methanol, ethanol, isopropyl alcohol, water, propanol, C4-C6 hydrocarbons, butane, isobutene, pentane, hexane, acetone, ethyl acetate, fluoro-chloro-hydrocarbons, methyl ethyl ketone, methyl ether, hydrofluorocarbons, ethyl ether, 1,1,1,2 tetrafluorethane 1,1,1,2,3,3,3-heptafluoropropane, 1,1,1,3,3,3 hexafluoropropane, or combinations thereof.

"Non-volatile solvent system" can be a single solvent or mixture of solvents that are less volatile than water. It can also contain substances that are solid or liquid at room temperatures, such as pH or ion-pairing agents. After evaporation of the volatile solvent system, most of the non-volatile solvent system should remain in the solidified layer for an amount of time sufficient to dermally delivery a given drug to, into, or through the skin of a subject at a sufficient flux for a period of time to provide a therapeutic effect. In some embodiments, in order to obtain desired permeability for an active drug and/or compatibility with solidifying agents or other ingredients of the formulation, a mixture of two or more non-volatile solvents can be used to form the non-volatile solvent system. In one embodiment, the combination of two or more non-volatile solvents to form a solvent system provides a higher transdermal flux for a drug than the flux provided for the drug by each of the non-volatile solvents individually. The non-volatile solvent system may also serve as a plasticizer of the solidified layer, so that the solidified layer is elastic and flexible. Different drugs may require different flux-enabling non-volatile solvent systems. For example, two flux-enabling non-volatile solvent systems for betamethasone dipropionate are propylene glycol and sorbitan monolaurate. Triacetin and oleic acid are not "flux-enabling" for betamethasone dipropionate. Similarly a mixture of propylene glycol and isostearic acid is a flux-enabling non-volatile solvent system for clobetasol propionate while propylene glycol alone or ethyl oleate are not.

The term "solvent vehicle" describes compositions that include both a volatile solvent system and non-volatile solvent system. The volatile solvent system is chosen so as to evaporate from the adhesive peelable formulation quickly to form a solidified layer, and the non-volatile solvent system is formulated or chosen to substantially remain as part of the solidified layer after volatile solvent system evaporation so as to provide continued delivery of the drug. Typically, the drug can be partially or completely dissolved in the solvent vehicle or formulation as a whole. Likewise, the drug can also be partially or completely solubilizable in the non-volatile solvent system once the volatile solvent system is evaporated. Formulations in which the drug is only partially dissolved in the non-volatile solvent system after the evaporation of the volatile solvent system have the potential to maintain longer duration of sustained delivery, as the undissolved drug can dissolve into the non-volatile solvent system as the dissolved drug is being depleted from the solidified layer during drug delivery.

"Adhesive solidifying formulation" or "solidifying formulation" refers to a composition that has a viscosity suitable for application to a skin surface prior to evaporation of its volatile solvent(s), and which can become a solidified layer after evaporation of at least a portion of the volatile solvent(s). The solidified layer, once formed, can be very durable. In one embodiment, once solidified on a skin surface, the formulation can form a peel. The peel can be a soft, coherent solid that can be removed by peeling large pieces from the skin relative to the size of the applied formulation, and often, can be peeled from the skin as a single piece. The application viscosity is typically more viscous than a water-like liquid, but less viscous than a soft solid. Examples of preferred viscosities include materials that have consistencies similar to pastes, gels, ointments, and the like, e.g., viscous liquids that flow but are not subject to spilling. Thus, when a composition is said to have a viscosity "suitable for application" to a skin surface, this means the composition has a viscosity that is high enough so that the composition does not substantially run off the skin after being applied to skin, but also has a low enough viscosity so that it can be easily spread onto the skin. A viscosity range that meets this definition can be from about 100 cP to about 3,000,000 cP (centipoises), and more preferably from about 1,000 cP to about 1,000,000 cP.

In some embodiments of the present invention, it may be desirable to add an additional agent or substance to the formulation so as to provide enhanced or increased adhesive characteristics. The additional adhesive agent or substance can be an additional non-volatile solvent or an additional solidifying agent. Non-limiting examples of substances which might be used as additional adhesion enhancing agents include copolymers of methylvinyl ether and maleic anhydride (Gantrez polymers), polyethylene glycol and polyvinyl pyrrolidone, gelatin, low molecular weight polyisobutylene rubber, copolymer of acrylsan alkyl/octylacrylamido (Dermacryl 79), and various aliphatic resins and aromatic resins.

The terms "washable," "washing" or "removed by washing" when used with respect to the solidified layers of the present invention refers to the ability of the solidified layer to be removed by the application of a washing solvent using a normal or medium amount of washing force. The required force to remove the solidified layer by washing should not cause significant skin irritation or abrasion. Generally, gentle washing force accompanied by the application of an appropriate washing solvent is sufficient to remove the solidified layers disclosed herein. The solvents which can be used for removing by washing the formulations of the present invention are numerous, but preferably are chosen from commonly acceptable solvents including the volatile solvents listed herein. Preferred washing solvents do not significantly irritate human skin and are generally available to the average subject. Examples of washing solvents include but are not limited to water, ethanol, methanol, isopropyl alcohol, acetone, ethyl acetate, propanol, or combinations thereof. In aspect of the invention the washing solvents can be selected from the group consisting of water, ethanol, isopropyl alcohol or combinations thereof. Surfactants can also be used in some embodiments.

An acceptable length of time for "drying time" refers to the time it takes for the formulation to form a non-messy solidified surface after application on skin under standard skin and ambient conditions, and with standard testing procedure. It is noted that the word "drying time" in this application does not mean the time it takes to completely evaporate off the volatile solvent(s). Instead, it means the time it takes to form the non-messy solidified surface as described above.

"Standard skin" is defined as dry, healthy human skin with a surface temperature of between about 30° C. to about 36° C. Standard ambient conditions are defined by the temperature range of from 20° C. to 25° C. and a relative humidity range of from 20% to 80%. The term "standard skin" in no way limits the types of skin or skin conditions on which the formulations of the present invention can be used. The formulations of the present invention can be used to treat all types of "skin," including undamaged (standard skin), diseased skin, or damaged skin. Although skin conditions having different characteristics can be treated using the formulations of the present invention, the use of the term "standard skin" is used merely as a standard to test the compositions of the varying embodiments of the present invention. As a practical matter, formulations that perform well (e.g., solidify, provide therapeutically effective flux, etc.) on standard skin can also perform well diseased or damaged skin.

The "standard testing procedure" or "standard testing condition" is as follows: To standard skin at standard ambient conditions is applied an approximately 0.1 mm layer of the adhesive solidifying formulation and the drying time is measured. The drying time is defined as the time it takes for the formulation to form a non-messy surface such that the formulation does not lose mass by adhesion to a piece of 100% cotton cloth pressed onto the formulation surface with a pressure of between about 5 and about 10 g/cm$^2$ for 5 seconds.

"Solidified layer" describes the solidified or dried layer of an adhesive solidifying formulation after at least a portion of the volatile solvent system has evaporated. The solidified layer remains adhered to the skin, and is preferably capable of maintaining good contact with the subject's skin for substantially the entire duration of application under standard skin and ambient conditions. The solidified layer also preferably exhibits sufficient tensile strength so that it can be peeled off the skin at the end of the application in one piece or several large pieces (as opposed to a layer with weak tensile strength that breaks into many small pieces or crumbles when removed from the skin).

As used herein, a plurality of drugs, compounds, and/or solvents may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. This same principle applies to ranges reciting only one numerical value. Furthermore, such an interpretation should apply regardless of the breadth of the range or the characteristics being described.

With these definitions in mind, a formulation for treating dermatitis or psoriasis can comprise a drug suitable for treating dermatitis or psoriasis, a solvent vehicle, and a solidifying agent. The solvent vehicle can include a volatile solvent system including one or more volatile solvents, and a non-volatile solvent system including one or more non-volatile solvents. The non-volatile solvent system can be capable of facilitating the delivery of the drug into the tissues to be treated at a therapeutically effective rate over a sustained period of time. The formulation can have a viscosity which is suitable for application and adhesion to a skin surface prior to evaporation of the volatile solvent system. Upon application to the skin surface as a layer, the formulation can form a solidified layer after at least partial evaporation of the volatile solvent system, and can continue to deliver drug after the volatile solvent system is at least substantially evaporated.

In an alternative embodiment, a method of dermally delivering a drug topically for treating dermatitis or psoriasis can include applying an adhesive solidifying formulation to a skin surface of a human suffering from dermatitis or psoriasis (such as hand dermatitis). The adhesive solidifying formulation can comprise a drug effective for treating dermatitis or psoriasis, a solvent vehicle, and a solidifying agent. The solvent vehicle can comprise a volatile solvent system including at least one volatile solvent, and a non-volatile solvent system including at least one non-volatile solvent, wherein the non-volatile solvent system is preferably capable of facilitating delivery of the drug at therapeutically effective rates over a sustained period of time. The formulation can have a viscosity suitable for application and adhesion to the skin surface as a layer prior to evaporation of the volatile solvent system. Additional steps include solidifying the formulation to form a solidified layer on the skin surface by at least partial evaporation of the volatile solvent system; and dermally delivering the drug from the solidified layer to or across the skin at therapeutically effective rates for treating the dermatitis or psoriasis over a sustained period of time.

In another embodiment, a solidified layer for delivering a drug for treating dermatitis or psoriasis can comprise a drug effective for treating dermatitis or psoriasis; a non-volatile solvent system including at least one non-volatile solvent, wherein the non-volatile solvent system is capable of facilitating the delivery of the drug at therapeutically effective rates over a sustained period of time; and a solidifying agent. The solidified layer can have such degree of flexibility, cohesion, elasticity, and adhesion to skin, that it does not substantially separate from the skin surface to which the layer is applied for substantially the entire duration of the intended application time.

In another embodiment, a formulation for treating dermatitis or psoriasis (such as hand dermatitis) can comprise a drug, a solvent vehicle, and a solidifying agent. The drug can include at least one member selected from the group consisting of clobetasol propionate, clobetasol, derivatives thereof, or combinations thereof. The volatile solvent system can include at least one volatile solvent, and a non-volatile solvent system including propylene glycol and/or glycerol, and another non-volatile solvent including isostearic acid and/or oleic acid. The solidifying agent can include at least one member selected from the group consisting of polyvinyl alcohol, fish gelatin, zein, or combinations thereof. The formulation can have a viscosity suitable for application and adhesion to a skin surface prior to evaporation of the volatile solvent system. The formulation applied to the skin surface can form a solidified, coherent, flexible, and continuous layer after at least partial evaporation of the volatile solvent system. Additionally, the drug can continue to be delivered at the therapeutically effective rate after the volatile solvent system is at least substantially all evaporated While the formulations, methods, and solidified layers of the current invention can be used to treat dermatitis (eczema) or psoriasis of skin areas anywhere on the human body, the special characteristics of the formulations and methods of the current invention are expected to be particularly beneficial for treating hand dermatitis and psoriasis.

In further detail, the present invention is related to novel formulations, methods, and solidified layers that are typically in the initial form of semi-solids (including creams, gels, pastes, ointments, and other viscous liquids), which can be easily applied onto the skin as a layer, and can, after the evaporation of at least some of the volatile solvent(s), quickly (from 15 seconds to about 4 minutes under standard skin and ambient conditions) to moderately quickly (from about 4 to about 15 minutes under standard skin and ambient conditions) change into a solidified layer, e.g., a coherent and soft solid layer which is optionally peelable, for topical delivery of drug(s) for treating skin disorders including dermatitis or psoriasis. The solidified layer, thus formed is capable of delivering drug over a sustained period of time, e.g., 30 minutes to tens of hours, so that most of the drug delivery takes place after the solidified layer is formed. Additionally, the solidified layer typically adheres to the skin, but has a solidified, minimally-adhering, outer surface which is formed relatively soon after application and which does not substantially transfer to or otherwise soil clothing or other objects that a subject is wearing or that the solidified layer may inadvertently contact. The solidified layer can also be formulated such that it is highly flexible and stretchable, and thus capable of maintaining good contact with a skin surface, even if the skin is stretched during body movement, such as at a knee, finger, palm of hand, sole of foot, elbow, or other joints. Sufficient contact time between the formulation and the skin can occur to deliver therapeutically effective amount of the drug. In one embodiment, the formulation is left on the skin surface for about 2 to about 12 hours. In another embodiment, the formulation is left on the skin surface for at least about 12 hours.

In selecting or formulating the various components that can be used, e.g., drug, solvent vehicle of volatile solvent system and non-volatile solvent system, solidifying agent(s), etc., various considerations can occur. For example, the volatile solvent system can be selected from pharmaceutically or cosmetically acceptable solvents known in the art. In one embodiment of the present invention, the volatile solvent system can include ethanol, isopropyl alcohol, water, dimethyl ether, diethyl ether, butane, propane, isobutene, 1,1, difluoroethane, 1,1,1,2 tetrafluorethane, 1,1,1,2,3,3,3-heptafluoropropane, 1,1,1,3,3,3 hexafluoropropane, ethyl acetate, acetone or combinations thereof. In another embodiment of the present invention, the volatile solvent system can include denatured alcohol, methanol, propanol, isobutene, pentane, hexane, methyl ethyl ketone, or combinations thereof. The volatile solvent system can include a mixture or combination of any of the volatile solvents set forth in the embodiments above.

These volatile solvents should be chosen to be compatible with the rest of the formulation. It is desirable to use an appropriate weight percentage of the volatile solvent(s) in the formulation. Too much of the volatile solvent system prolongs the drying time. Too little of the volatile solvent system can make it difficult to spread the formulation on the skin. For most formulations, the weight percentage of the volatile solvent(s) can be from about 10 wt % to about 85 wt %, from about 20 wt % to about 50 wt %, and in a preferred embodiment, at least 20 wt %.

The volatile solvent system can also be chosen to be compatible with the non-volatile solvent, solidifying agent, drug, and any other excipients that may be present. For example, polyvinyl alcohol (PVA) is not soluble in ethanol. Therefore, a volatile solvent which can dissolve PVA needs to be formulated in the solidified layer. For instance, water can dissolve PVA and can be utilized as a volatile solvent in a solidifying formulation; however, the drying time in a formulation in which water is the only volatile solvent may be too long to certain applications. Therefore, a second volatile solvent, e.g., ethanol, can be formulated into the formulation to reduce the water content but maintain a sufficient amount of water to keep PVA in solution and thereby reduce the drying time for the formulation.

The non-volatile solvent system can also be chosen or formulated to be compatible with the solidifying agent, the drug, the volatile solvent, and any other ingredients that may be present. For example, the solidifying agent can be chosen so that it is dispersible or soluble in the non-volatile solvent system. Most non-volatile solvent systems and solvent vehicles as a whole will be formulated appropriately after experimentation. For instance, certain drugs have good solubility in poly ethylene glycol (PEG) having a molecular weight of 400 (PEG 400, non-volatile solvent) but poor solubility in glycerol (non-volatile solvent) and water (volatile solvent). However, PEG 400 cannot effectively dissolve poly vinyl alcohol (PVA), and thus, is not very compatible alone with PVA, a solidifying agent. In order to dissolve sufficient amount of an active drug and use PVA as a solidifying agent at the same time, a non-solvent system including PEG 400 and glycerol (compatible with PVA) in an appropriate ratio can be formulated, achieving a compatibility compromise. As a further example of compatibility, non-volatile solvent/solidifying agent incompatibility is observed when Span 20 is formulated into a solidifying formulation containing PVA. With this combination, Span 20 can separate out of the formulation and form an oily layer on the surface of the solidified layer. Thus, appropriate solidifying agent/non-volatile solvent selections are desirable in developing a viable formulation and compatible combinations.

This being stated, non-volatile solvent(s) that can be used alone or in combination to form non-volatile solvent systems can be selected from a variety of pharmaceutically acceptable liquids. In one embodiment of the present invention the non-volatile solvent system can include glycerol, propylene glycol, isostearic acid, oleic acid, propylene glycol, trolamine, tromethamine, triacetin, sorbitan monolaurate, sorbitan monooleate, sorbitan monopalmitate, or combinations thereof. In another embodiment the non-volatile solvent system can include benzoic acid, dibutyl sebecate, diglycerides, dipropylene glycol, eugenol, fatty acids such as coconut oil, fish oil, palm oil, grape seed oil, isopropyl myristate, mineral oil, oleyl alcohol, vitamin E, triglycerides, sorbitan fatty acid surfactants, triethyl citrate, or combinations thereof. In a further embodiment the non-volatile solvent system can include 1,2,6-hexanetriol, alkyltriols, alkyldiols, tocopherol, p propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, cocoglycerides, corn oil, coriander oil, corn syrup, cottonseed oil, cresol, diacetin, diacetylated monoglycerides, diethanolamine, diglycerides, ethylene glycol, eucalyptus oil, fat, fatty alcohols, flavors, liquid sugars ginger extract, glycerin, high fructose corn syrup, hydrogenated castor oil, IP palmitate, lemon oil, lime oil, limonene, monoacetin, monoglycerides, nutmeg oil, octyldodecanol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG Fatty acid esters such as PEG-stearate, PEG-oleate, PEG-laurate, PEG fatty acid diesters such as PEG-dioleate, PEG-distearate, PEG-castor oil, glyceryl behenate, PEG glycerol fatty acid esters such as PEG glyceryl laurate, PEG glyceryl stearate, PEG glyceryl oleate, hexylene glycerol, lanolin, lauric diethanolamide, lauryl lactate, lauryl sulfate, medronic acid, multisterol extract, myristyl alcohol, neutral oil, PEG-octyl phenyl ether, PEG-alkyl ethers such as PEG-cetyl ether, PEG-stearyl ether, PEG-sorbitan fatty acid esters such as PEG-sorbitan diisosterate, PEG-sorbitan monostearate, propylene glycol fatty acid esters such as propylene glycol stearate, propylene glycol, caprylate/caprate, sodium pyrrolidone carboxylate, sorbitol, squalene, stear-o-wet, triglycerides, alkyl aryl polyether alcohols, polyoxyethylene derivatives of sorbitan-ethers, saturated polyglycolyzed C8-C10 glycerides, N-methylpyrrolidone, honey, polyoxyethylated glycerides, dimethyl sulfoxide, azone and related compounds, dimethylformamide, N-methyl formamaide, fatty acid esters, fatty alcohol ethers, alkyl-amides (N,N-dimethylalkylamides), N-methylpyrrolidone related compounds, ethyl oleate, polyglycerized fatty acids, glycerol monooleate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, limnanthes alba seed oil, cetearyl alcohol, PEG-50 shea butter, shea butter, aloe vera juice, phenyl trimethicone, hydrolyzed wheat protein, or combinations thereof. In yet a further embodiment the non-volatile solvent system can include a combination or mixture of non-volatile solvents set forth in the any of the above discussed embodiments.

For preferred embodiments, the non-volatile solvent(s) should be selected or formulated to qualify as "adequate non-volatile solvent(s)" as defined above. In addition to these and other considerations, the non-volatile solvent system can also serve as plasticizer in the adhesive peelable formulation so that when the solidified layer is formed, the layer is flexible, stretchable, and/or otherwise skin friendly.

Certain volatile and/or nonvolatile solvent(s) that are irritating to the skin, but may be otherwise desirable to use to achieve the desired solubility and/or permeability of the drug, can be used as well. It can also be desirable to add compounds that are both capable of preventing or reducing skin irritation and are compatible with the formulation. For example, in a formulation where the volatile solvent is capable of irritating the skin, it would be helpful to use a non-volatile solvent that is capable of reducing skin irritation. Examples of non-volatile solvents that are capable of preventing or reducing skin irritation include, but are not limited to, glycerin, honey, and/or propylene glycol.

The formulations of the present invention can also contain ion-paring agents such as bases and acids. The purpose of these agent(s) is to optimize the ionization state of the drug for obtaining desired delivery rates or to optimize the pH of the formulation or the skin tissues under the formulation layer to minimize irritation. Examples of suitable ion-pairing agents include, but are not limited to trolamine, diisopropylamine, hydrochloric acid, sodium hydroxide, acetic acid, and neutrol TE.

The selection of the solidifying agent can also be carried out in consideration of the other components present in the adhesive formulation. An appropriate solidifying agent is compatible with the formulation such that the formulation is in liquid or semi-liquid state (e.g. cream, pastep, gel, ointment) before any evaporation of the volatile solvent(s) and becomes a soft, coherent solid after the evaporation of at least some of the volatile solvent(s). The solidifying agent can be selected or formulated to be compatible with the drug and the solvent vehicle (including the volatile solvent(s) and the non-volatile solvent system), as well as provide desired physical properties to the solidified layer once it is formed. Depending on the drug, solvent vehicle, and/or other components that may be present, the solidifying agent can be selected from a variety of agents. In one embodiment, the solidifying agent can include polyvinyl alcohol with a MW range of 20,000-70,000 (Amresco), esters of polyvinylmethylether/maleic anhydride copolymer (ISP Gantrez ES-425 and Gantrez ES-225) with a MW range of 80,000-160,000, neutral copolymer of butyl methacrylate and methyl methacrylate (Degussa Plastoid B) with a MW range of 120,000-180,000, dimethylaminoethyl methacrylate-butyl methacrylate-methyl methacrylate copolymer (Degussa Eudragit E100) with a MW range of 100,000-200,000, ethyl acrylate-methyl methacrylate-trimethylammonioethyl methacrylate chloride copolymer with a MW greater than 5,000 or similar MW to Eudragit RLPO (Degussa), Zein (prolamine) with a MW greater than 5,000 such as Zein with a MW around 35,000 (Freeman industries), pregelatinized starch having a MW similar to Instant Pure-Cote B793 (Grain Processing Corporation), ethyl cellulose MW greater than 5,000 or MW similar to Aqualon EC N7, N10, N14, N22, N50, or N100 (Hercules), fish gelatin having a MW 20,000-250,000 (Norland Products), gelatin, other animal sources with MW greater than 5,000, acrylates/octylacrylamide copolymer MW greater than 5,000 or MW similar to National Starch, or Chemical Dermacryl 79.

In another embodiment the solidifying agent can include ethyl cellulose, hydroxy ethyl cellulose, hydroxy methyl cellulose, hydroxy propyl cellulose, hydroxypropyl methyl cellulose, carboxymethyl cellulose, methyl cellulose, polyether amides, corn starch, pregelatinized corn starch, polyether amides, shellac, polyvinyl pyrrolidone, polyisobutylene rubber, polyvinyl acetate phthalate or combinations thereof. In a further embodiment the solidifying agent can include ammonia methacrylate, carrageenan, cellulose acetate phthalate aqueous such as CAPNF from Eastman, carboxy polymethylene, cellulose acetate (microcrystalline), cellulose polymers, divinyl benzene styrene, ethylene vinyl acetate, silicone, guar gum, guar rosin, gluten, casein, calcium caseinate, ammonium caseinate, sodium caseinate, potassium caseinate, methyl acrylate, microcrystalline wax, polyvinyl acetate, PVP ethyl cellulose, acrylate, PEG/PVP, xantham gum, trimethyl siloxysilicate, maleic acid/anhydride colymers, polacrilin, poloxamer, polyethylene oxide, poly glactic acid/poly-1-lactic acid, turpene resin, locust bean gum, acrylic copolymers, polyurethane dispersions, dextrin, polyvinyl alcohol-polyethylene glycol co-polymers, methyacrylic acid-ethyl acrylate copolymers such as BASF's Kollicoat polymers, methacrylic acid and methacrylate based polymers such as poly(methacrylic acid), or combinations thereof. In another embodiment, the solidifying agent can include a combination of solidifying agents set forth in the any of the above discussed embodiments. Other polymers may also be suitable as the solidifying agent, depending on the solvent vehicle components, the drug, and the specific functional requirements of the given formulation. Other polymers may also be suitable as the solidifying agent, depending on the solvent vehicle components, the drug, and the specific functional requirements of the given formulation.

In some embodiments of the present invention, it may be desirable to add an additional agent or substance to the formulation so as to provide enhanced or increased adhesive characteristics. The additional adhesive agent or substance can be an additional non-volatile solvent or an additional solidifying agent. Non-limiting examples of substances which might be used as additional adhesion enhancing agents include copolymers of methylvinyl ether and maleic anhydride (Gantrez polymers), polyethylene glycol and polyvinyl pyrrolidone, gelatin, low molecular weight polyisobutylene rubber, copolymer of acrylsan alkyl/octylacrylamido (Dermacryl 79), and various aliphatic and aromatic resins.

The non-volatile solvent system and the solidifying agent should be compatible with each other. Compatibility is defined as i) the solidifying agent does not substantially negatively influence the function of the non-volatile solvent system; ii) the solidifying agent can hold the non-volatile solvent system in the solidified layer so that substantially no non-volatile solvent oozes out of the layer, and/or iii) the solidified layer formed with the selected non-volatile solvent system and the solidifying agent has acceptable flexibility, rigidity, tensile strength, elasticity, and adhesiveness to skin. The weight ratio of the non-volatile solvent system to the solidifying agent can be from about 0.1:1 to about 10:1. In another aspect, the weight ratio of the non-volatile solvent system to the solidifying agent can be from about 0.2:1 to about 4:1, and more preferably from about 0.5:1 to about 2:1.

To provide some practical parameters, typically, concentrations of active drugs in topical formulations rarely exceed 10 wt % (by weight of active drug in weight of total formulation). In one embodiment, if the non-volatile solvent system of a formulation makes up 30 wt % of the total formulation weight, this means the concentration of the active drug in the non-volatile solvent system is about 25 wt %. In such a formulation, the permeation driving force will be significantly reduced if the solubility of the non-volatile solvent system for the drug is much higher than 25 wt %. The maximum drug concentrations in many physically and commercially viable products are significantly less than 10 wt %, which in turn means the upper limits of the window of operable solubility are significantly lower for those systems, more likely in the 1 wt % to 10 wt % range.

The thickness of the formulation layer applied on the skin should also be appropriate for a given formulation and desired drug delivery considerations. If the layer is too thin, the amount of the drug may not be sufficient to support sustained delivery over the desired length of time. If the layer is too thick, it may take too long to form a non-messy outer surface of the solidified layer. If the drug is very potent and the solidified layer has very high tensile strength, a layer as thin as about 0.01 mm may be sufficient. If the drug has rather low potency and the solidified layer has low tensile strength, a layer as thick as about 2-3 mm maybe needed. Thus, for most drugs and formulations, the appropriate thickness can be from about 0.01 mm to about 3 mm, but more typically, from about 0.05 mm to about 1 mm.

Flexibility and stretchability of the solidified layer, which is optionally also a peelable, can be desirable in some applications. High tolerance for flex and stretch are particularly advantageous when the area of skin being treated is on the hands, feet, or other area of skin involved in frequent movement such as a joint. As mentioned previously, skin disorders are often manifested on the hands due to their frequent contact with irritating substances. Traditional lotions, ointments, creams, gels, pastes or the like are often not suitable for treatment of these areas because they are easily removed by contact with clothing or other surfaces. In contrast, the solidifying compositions of the present invention can be formulated so as to provide adequate flexibility and stretching while not being easily rubbed or scraped off. It is also worth noting that the solidified layers of the present invention do not always need to be stretchable.

A further feature of the formulation of the present invention is related to the drying time. If a formulation dries too quickly, the user may not have sufficient time to spread the formulation into a thin layer on the skin surface before the formulation is solidified, leading to poor skin contact. If the formulation dries too slowly, the subject may have to wait a long time before resuming normal activities (e.g. putting clothing on, working, etc.) that may remove un-solidified formulation. Thus, it is desirable that the drying time of the formulation under standard skin and ambient conditions be longer than about 15 seconds but shorter than about 15 minutes, and preferably from about 0.5 minutes to about 5 minutes.

Another feature of the formulations of the present invention is related to solidifying formulations comprising a drug for controlling neuropathic pain, a non-volatile solvent system comprising at least one non-volatile solvent, a solidifying agent, and a volatile solvent system comprising a volatile solvent whose boiling point is below 20° C. (such a solvent can be used as a propellant or can be dissolved in the formulation). In one embodiment, the formulation can be stored in a pressurized container and be sprayed on the skin surface with the help of the propellant. Some hydrofluorocarbons commonly used as propellants in pharmaceutical or dosmetic industries can work in this design. More specifically, the propellants may include, but not limited to dimethyl ether, butane, 1,1, Difluoroethane, 1,1,1,2 tetrafluorethane, 1,1,1,2,3,3,3-heptafluoropropane, 1,1,1,3,3,3 hexafluoropropane, or a mixture thereof. The formulation may also be expelled out of the container and applied on the skin via a manual pump. Formulations comprising a these room temperature gaseous volatile solvents are expected to dry much faster. Spraying the formulation onto the skin suffering from neuropathic pain can avoid touching the skin with an applicator which can cause severe pain in the sometimes hypersensitive skin.

The formulations of the current invention may further comprise a pH modifying agent for adjusting the pH of the formulation to a point or a range most suitable for the delivery of the drug. This feature can be important for a drug that is ionizable.

Other benefits of the solidified layers of the present invention include the presence of a physical barrier that can be formed by the material itself. This barrier can insulate the skin from substances that can irritate the diseased skin or that can cause or trigger dermatitis or psoriasis. These and other advantages can be summarized as follows. The solidifying formulations of the present invention can be prepared in an initial form that is easy to apply as a semisolid dosage form. After the evaporation of the volatile solvent(s) and the formation of the solidified layer, the drug in the remaining non-volatile solvent system (which is in the solidified layer) can provide desired delivery rates of the drug over sustained periods of time. Further, as the solidified layer remains adhered to skin and often are peelable, easy removal of the solidified layer can occur, usually without the aid of a solvent or surfactant. This being described, certain embodiments benefit from removal of the formulation by a solvent, particularly if the skin is severely diseased and would be damaged by mechanical peeling of the formulation The adhesion to skin and elasticity of the material is preferably such that the solidified layer will not easily separate from the skin during the application. For example, in one embodiment, the solidified layer can be stretched in at least one direction by up to about 5% or even 10% or more without cracking, breaking, or separating form a skin surface to which the formulation was applied. Specific examples of applications that can benefit from the systems, formulations, and methods of the present invention are as follows. In one embodiment, a solidified layer including corticosteroid such as clobetasol propionate can be formulated for treating hand dermatitis. Alternatively, immune modulators, such as tacrolimus, can be formulated in a solidifying formulation for treating psoriasis on the hand skin. In another embodiment, retinoic acids, such as tazarotene or vitamin D3 derivatives, can be formulated in a solidifying formulation for treating the same diseases.

As a further note, it is a unique feature of the solidified layers of the present invention that they can keep a substantial amount of the non-volatile solvent system, which is optimized for delivering the drug, on the body surface. This feature can provide unique advantages over existing products. For example, in some semi-solid formulations, upon application to a skin surface the volatile solvents quickly evaporate and the formulation layer solidifies into a hard lacquer-like layer. The drug molecules are immobilized in the hard lacquer layer and are substantially unavailable for delivery into the skin surface. As a result, it is believed that the delivery of the drug is not sustained over a long period of time. In contrast to this type of formulation, the solidified layers formed using the formulations of the present invention keep the drug molecules quite mobile in the non-volatile solvent system which is in contact with the skin surface, thus ensuring sustained delivery.

Non-limiting classes of drugs which can be used in the formulations of the present invention include corticosteroids, immune modulators, analogs of vitamin D3, retinoic acids, pharmaceutically active derivatives thereof or combinations thereof. examples of drugs which can be delivered using the formulations of the present invention include but are not limited to betamethasone dipropionate, clobetasol propionate, halobetasol propionate, diflorasone diacetate, amcinonide, desoximethasone, fluocinonide, halcinonide, mometasone furoate, betamethasone valerate, fluocinonide, fluticasone propionate, triamcinolone acetonide, fluocinolone acetonide, flurandrenolide, desonide, hydrocortisone butyrate, hydrocortisone valerate, alclometasone dipropionate, flumethasone pivolate, hydrocortisone, hydrocortisone acetate, tacrolimus, picrolimus, tazarotene, isotretinoin, cyclosporin, anthralin, vitamin D3, cholecalciferol, calcitriol, calcipotriol, tacalcitol, calcipotriene, or combinations thereof.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Hairless mouse skin (HMS) or human epidermal membrane (HEM) is used as the model membranes as noted for the in vitro flux studies described in herein. Hairless mouse skin (HMS) is used as the model membrane for the in vitro flux studies described in herein. Freshly separated epidermis removed from the abdomen of a hairless mouse is mounted carefully between the donor and receiver chambers of a Franz diffusion cell. The receiver chamber is filled with pH 7.4 phosphate buffered saline (PBS). The experiment is initiated by placing test formulations (of Examples 2-5) on the stratum corneum (SC) of the skin sample. Franz cells are placed in a heating block maintained at 37° C. and the HMS temperature is maintained at 35° C. At predetermined time intervals, 800 µL aliquots are withdrawn and replaced with fresh PBS solution. Skin flux ($\mu g/cm^2/h$) is determined from the steady-state slope of a plot of the cumulative amount of permeation versus time. It is to be noted that human cadaver skin can be used as the model membrane for the in vitro flux studies as well. The mounting of the skin and the sampling techniques used as the same as described above for the HMS studies.

Example 2

Formulations of betamethasone dipropionate (BDP) in various non-volatile solvent systems are evaluated following procedure described in Example 1. Excess BDP is present. The permeation of BDP from the test formulations through HEM is presented in Table 1 below.

TABLE 1

Non volatile solvents for betamethasone dipropionate

| Non-volatile solvent system | Skin Flux* (ng/cm$^2$/h) |
|---|---|
| Propylene Glycol | 195.3 ± 68.5 |
| Triacetin | 4.6 ± 2.8 |
| Light Mineral Oil | 11.2 ± 3.1 |
| Oleic Acid | 8.8 ± 3.3 |
| Sorbitan Monolaurate | 30.0 ± 15.9 |
| Labrasol | 12.2 ± 6.0 |

*Skin flux measurements represent the mean and standard deviation of three determinations. Flux measurements reported were determined from the linear region of the cumulative amount versus time plots. The linear region was observed to be between 6–28 hours. If the experiment was continued it is anticipated the steady state would continue.

Active enzymes in the skin convert BDP to betamethasone. The steady state flux values reported in Table 1 are quantified using external betamethasone standards and are reported as amount of betamethasone permeating per unit area and time. As seen from the results triacetin, labrasol, oleic acid, and light mineral oil have flux values close to 10 ng/cm2/hr. Addition of solidifying agents and other components could possibly decrease the flux and therefore the above mentioned solvents would not be an ideal non-volatile solvent. However, sorbitan monolaurate and propylene glycol have average flux of 30 ng/cm$^2$/hr and 195 ng/cm$^2$/hr, respectively, and therefore are good candidates for non-volatile solvent.

Example 3

Formulations of clobetasol propionate in various non-volatile solvent systems are evaluated. All solvents have 0.1% (w/w) clobetasol propionate. The permeation of clobetasol from the test formulations through HEM is presented in Table 2 below.

TABLE 2

Non volatile solvents for clobetasol propionate

| Non-volatile solvent system | Skin Flux* (ng/cm$^2$/h) |
|---|---|
| Propylene Glycol | 3.8 ± 0.4 |
| Glycerol | 7.0 ± 4.1 |
| Light Mineral Oil | 31.2 ± 3.4 |
| Isostearic Acid (ISA) | 19.4 ± 3.2 |
| Ethyl Oleate | 19.4 ± 1.6 |
| Olive Oil | 13.6 ± 3.3 |
| Propylene Glycol/ISA (9:1) | 764.7 ± 193.9 |

*Skin flux measurements represent the mean and standard deviation of three determinations. Flux measurements reported were determined from the linear region of the cumulative amount versus time plots. The linear region was observed to be between 6–28 hours. If the experiment was continued it is anticipated the steady state would continue.

All the pure non-volatile solvents studied have an average flux of less than 40 ng/cm2/hr over the 30 hour time period. Propylene glycol and glycerol have the lowest permeation for clobetasol propionate. A mixture of propylene glycol and isostearic acid in weight ratio of 9:1 have significantly higher flux than either of the solvents alone or the other solvents tested. The average flux is 20 times higher than that with light mineral oil which is the best non-mixed solvent. Hence, for clobetasol propionate propylene glycol/isostearic acid combination is an ideal non-volatile solvent.

Examples 4-9

Adhesive solidifying formulations containing 0.05% (w/w) clobetasol propionate with propylene glycol and isostearic acid as non volatile solutions and various solidifying agents are prepared. The formulations are prepared from the ingredients as shown in Table 3.

TABLE 3

Solidifying formulation components

| Example | Polymer | Percent Polymer | Percent Ethanol | Percent Propylene Glycol | Percent Isostearic Acid | Percent Water |
|---|---|---|---|---|---|---|
| 4 | Polyvinyl Alcohol | 20 | 30 | 19.6 | 0.4 | 30 |
| 5 | Shellac | 50 | 30 | 19.6 | 0.4 | 0 |
| 6 | Dermacryl 79 | 65.76 | 21.16 | 12.76 | 0.26 | 0 |
| 7 | Eudragit E100 | 50 | 30 | 19.6 | 0.40 | 0 |
| 8 | Eudragit RLPO | 50 | 30 | 19.6 | 0.40 | 0 |
| 9 | Gantrez S97 | 14.3 | 57.1 | 28 | 0.6 | 0 |

Each of the compositions shown above are studied for flux of clobetasol propionate as shown in Table 4 as follows:

TABLE 4

Steady state flux of clobetasol propionate through human cadaver skin at 35° C.

| Formulation | Skin Flux* (ng/cm$^2$/h) |
|---|---|
| Example 4 | 87.8 ± 21.4 |
| Example 5 | 9.7 ± 2.4 |
| Example 6 | 8.9 ± 0.8 |
| Example 7 | 3.2 ± 1.7 |
| Example 8 | 20.2 ± 18.6 |
| Example 9 | 147.5 ± 38.8 |

*Skin flux measurements represent the mean and standard deviation of three determinations. Flux measurements reported were determined from the linear region of the cumulative amount versus time plots. The linear region was observed to be between 6–28 hours. If the experiment was continued it is anticipated the steady state would continue.

As seen from Table 4 formulation described in Example 4 that contains polyvinyl alcohol as solidifying agents has high flux of clobetasol propionate. Polyvinyl alcohol is known to form stretchable films (if formulated with appropriate plasticizer) and it is likely that this formulation will have acceptable wear properties. The toughness of the resulting film can be modified by adding appropriate plasticizers if needed. Tackiness can also be modified by adding appropriate amounts of tackifier or by adding appropriate amounts of another solidifying agent such as dermacryl 79.

Regarding formulation described in Example 9, a higher percentage of ethanol is needed to dissolve the polymer. However, the polymer used in Example 9 provides the highest flux of clobetasol propionate among the solidifying agents studied. The wear properties of this formulation can be modified by adding appropriate levels of other ingredients including but not limited to plasticizers, tackifiers, non-volatile solvents and or solidifying agents.

Examples 10-12

Placebo formulations containing Gantrez ES 425 as a tackifier were prepared for wear studies by volunteers. The formulations are shown as examples in Table 5. All the formulations have Polyvinyl alcohol as the solidifying agent. The amount of propylene glycol in the formulations was decreased from 19.6% (w/w) to 8.7% (w/w), and the amount of glycerol was increased by the same amount to keep the total non-volatile ratio constant. Keeping the non-volatile ratio constant is important as it determines the drying time and the duration of delivery. The placebo formulations are worn on the palms of hand and percentage adherence of the film formed after evaporation of volatile solvents was observed after 5-6 hours.

TABLE 5

Placebo formulations (% w/w ingredients)

| Ingredient | Example 10 | Example 11 | Example 12 |
|---|---|---|---|
| Polyvinyl Alcohol | 21.7% | 21.7% | 21.7% |
| Water | 32.6% | 32.6% | 32.6% |
| Glycerol | 8.7% | 13.0% | 19.6% |
| Propylene Glycol | 19.6% | 15.2% | 8.7% |
| Gantrez ES 425 | 4.3% | 4.3% | 4.3% |
| Oleic acid | 4.3% | 4.3% | 4.3% |
| Ethanol | 8.7% | 8.7% | 8.7% |

Wear study results on 3 volunteers show that 70-80% of solidified layer as described in Example 10 stayed on palms after a duration of 5-6 hours. However, greater than 90% of solidified layer as shown in Example 12 stayed on palms of the volunteers. These examples demonstrate that glycerol is a better plasticizer that propylene glycol for the polyvinyl alcohol polymer. It also shows that the ratio of non-volatile solvent is critical in selecting the formulation for treatment of hand dermatitis.

Example 13

A formulation with the following composition: 10.4% polyvinyl alcohol, 10.4% polyethylene glycol 400, 10.4% polyvinyl pyrrolidone K-90, 10.4% glycerol, 27.1% water, and 31.3% ethanol was applied onto a human skin surface at an elbow joint and a finger joint, resulting in a thin, transparent, flexible, and stretchable film. After a few minutes of evaporation of the volatile solvents (ethanol and water), a solidified peelable layer that was peelable was formed. The stretchable film had good adhesion to the skin and did not separate from the skin on joints when bent, and could easily be peeled away from the skin.

Examples 14-15

Adhesive peelable formulations containing 0.05% (w/w) clobetasol propionate and 0.15% (w/w) clobetasol propionate with polyvinyl alcohol as solidifying polymer are prepared for in-vitro flux evaluation. Propylene glycol and oleic acid are the non volatile solvents selected for facilitation of clobetasol propionate delivery. As shown in Example 12, glycerol is added as the non volatile solvent for its plasticizing properties. Ratios of ingredients used in the two formulations are shown in Table 6.

TABLE 6

Clobetasol Propionate peel formulations*

| Ingredient | Example 14 | Example 15 |
|---|---|---|
| Polyvinyl Alcohol | 22.7% | 22.7% |
| Water | 34.1% | 34.0% |
| Glycerol | 17.3% | 17.2% |
| Propylene Glycol | 7.7% | 7.7% |
| Gantrez ES 425 | 4.5% | 4.5% |
| Oleic acid | 4.5% | 4.5% |
| Ethanol | 9.1% | 9.1% |
| Clobetasol Propionate | 0.05% | 0.15% |

*Numbers do not add to 100% because of rounding in the second decimal.

Both of the compositions shown above are studied for flux of clobetasol propionate on cadaver skin from three donors. The permeation results are as shown in Table 7. Commercial clobetasol ointment (0.05% w/w) was used as a control formulation.

TABLE 7

Steady state flux of clobetasol propionate through human cadaver skin at 35° C.

| Skin Donor | Control $J^*$ (ng/cm$^2$/h) | Example 14 $J^*$ (ng/cm$^2$/h) | Example 15 $J^*$ (ng/cm$^2$/h) |
|---|---|---|---|
| Donor 1 | 22.4 ± 2.1 | 8.8 ± 1.9 | 29.2 ± 8.2 |
| Donor 2 | 20.0 ± 2.5 | 7.6 ± 2.5 | 18.5 ± 6.4 |
| Donor 3 | 35.0 ± 4.7 | 19.3 ± 5.9 | 24.8 ± 7.7 |
| Mean +/− SD (n = 3 donors) | 25.8 ± 7.5 | 11.9 ± 6.5 | 24.2 ± 8.0 |

*Skin flux measurements represent the mean and standard deviation of three determinations. Flux measurements reported are determined from the linear region of the cumulative amount versus time plots. The linear region are observed to be between 6–28 hours. If the experiment is continued, it is anticipated the steady state would continue.

As seen from Table 7 formulation described in Example 14 that contained polyvinyl alcohol as a solidifying agent and 0.05% clobetasol propionate had 46% flux of clobetasol propionate when compared to the control formulation. Increasing the clobetasol propionate concentration drug concentration to 0.15% (w/w) increased the steady state flux and the flux values were 94% of the control formulation. It is expected that longer duration of application with the peel formulation would increase cumulative delivery in-vivo resulting in effective treatment of dermatitis.

Example 16

Adhesive solidifying formulations containing 0.05% (w/w) clobetasol propionate with fish gelatin as solidifying agent are prepared for in-vitro flux evaluation. Propylene glycol, isostearic acid, and oleic acid are used as non-volatile solvents to facilitate delivery of clobetasol. Talc is added as a filler to reduce the drying time the formulation. Ratio of ingredients used in the formulation is shown in Table 8.

TABLE 8

Clobetasol Propionate formulations*

| Ingredient | Example 16 |
|---|---|
| Fish Gelatin | 29.4% |
| Water | 22.0% |
| Ethanol | 14.7% |
| Propylene Glycol | 17.6% |

TABLE 8-continued

Clobetasol Propionate formulations*

| Ingredient | Example 16 |
| --- | --- |
| Isostearic acid | 2.2% |
| Oleic acid | 2.2% |
| Talc | 11.8% |
| Clobetasol Propionate | 0.05% |

*Numbers do not add to 100% because of rounding in the second decimal.

Unlike the polyvinyl based formulations shown in previous examples, the fish gelatin based formulation shown in Example 16 is a water washable formulation and can be easily removed by subjects suffering from hand dermatitis. Steady state flux across human cadaver skin from 3 donors with formulation as described in Example 16 is compared to the commercial clobetasol ointment. The permeation results are shown in Table 9.

TABLE 9

Steady state flux of clobetasol propionate through human cadaver skin at 35° C.

| Skin Donor | Control $J^*$ (ng/cm$^2$/h) | Example 16 $J^*$ (ng/cm$^2$/h) |
| --- | --- | --- |
| Donor 1 | 39.2 ± 9.2 | 46.1 ± 14.3 |
| Donor 2 | 35.6 ± 2.1 | 52.9 ± 22.3 |
| Donor 3 | 35.6 ± 5.7 | 79.7 ± 18.4 |
| Mean +/− SD (n = 3 donors) | 36.8 ± 5.8 | 59.6 ± 22.3 |

*Skin flux measurements represent the mean and standard deviation of three determinations. Flux measurements reported are determined from the linear region of the cumulative amount versus time plots. The linear region are observed to be between 6–28 hours. If the experiment is continued, it is anticipated the steady state would continue.

As seen from Table 9, formulation described in Example 16 has 62% higher steady state flux when compared to the commercial ointment. Higher steady state flux would is expected to reduce inflammation in difficult to treat dermatitis and psoriasis cases.

Example 17

Adhesive solidifying formulations containing 0.05% (w/w) clobetasol propionate with fish gelatin as solidifying polymer are prepared for in-vitro flux evaluation. Propylene glycol, and isostearic acid are used as non-volatile solvents to facilitate delivery of clobetasol. Fumed silica is added as a filler to reduce the drying time the formulation. Ratio of ingredients used in the formulation is shown in Table 10.

TABLE 10

Clobetasol Propionate formulations*

| Ingredient | Example 17 |
| --- | --- |
| Fish Gelatin | 32.2% |
| Water | 24.2% |
| Ethanol | 16.1% |
| Propylene Glycol | 19.3% |
| Isostearic acid | 4.8% |
| Fumed Silica | 3.2% |
| Clobetasol Propionate | 0.05% |

*Numbers do not add to 100% because of rounding in the second decimal.

The fish gelatin based formulation shown in Example 17 is a water washable formulation and can be easily removed by subjects suffering from hand dermatitis. Steady state flux across human cadaver skin from 4 donors with formulation as described in Example 17 is compared to the commercial clobetasol ointment. The permeation results are shown in Table 11.

TABLE 11

Steady state flux of clobetasol propionate through human cadaver skin at 35° C.

| Skin Donor | Control $J^*$ (ng/cm$^2$/h) | Example 17 $J^*$ (ng/cm$^2$/h) |
| --- | --- | --- |
| Donor 1 | 28.2 ± 7.8 | 20.7 ± 12.8 |
| Donor 2 | 30.1 ± 14.9 | 30.6 ± 13.8 |
| Donor 3 | 36.2 ± 6.2 | 93.4 ± 7.5 |
| Donor 4 | 33.6 ± 3.9 | 101.4 ± 8.5 |
| Mean +/− SD (n = 3 donors) | 32.0 ± 8.5 | 61.5 ± 38.9 |

*Skin flux measurements represent the mean and standard deviation of three determinations. Flux measurements reported are determined from the linear region of the cumulative amount versus time plots. The linear region are observed to be between 6–28 hours. If the experiment is continued, it is anticipated the steady state would continue.

As seen from Table 11, on an average, formulation described in Example 17 has at-least similar or better steady state flux when to compared to the steady state flux with the commercial ointment. Unlike talc used in Example 16, fumed silica had a low density and is expected to have a less potential to separate from the formulation.

Example 18

Example 16 and 17 indicate that fish gelatin, a protein based solidifying agent (polymer) based formulations is preferred polymer of choice for delivery of corticosteroid drugs. However, fish gelatin based formulations take a longer time to dry. Alternate adhesive formulations containing 0.05% (w/w) clobetasol propionate with zein, a corn based protein, as solidifying polymer are prepared for in-vitro flux evaluation. Propylene glycol, and isostearic acid are used as non-volatile solvents to facilitate delivery of clobetasol. Unlike fish gelatin, which has poor solubility in ethanol, zein, is soluble in ethanol, and hence zein based formulations have a lower drying time. Ratio of ingredients used in the formulation is shown in Table 12.

TABLE 12

Clobetasol Propionate formulations with zein*

| Ingredient | Example 18 |
| --- | --- |
| Zein | 36.3% |
| Propylene Glycol | 21.8% |
| Isostearic acid | 5.5% |
| Ethanol | 36.3% |
| Clobetasol Propionate | 0.05% |

*Numbers do not add to 100% because of rounding in the second decimal.

Steady state flux across human cadaver skin with formulation as described in Example 18 is compared to the skin flux with a commercial clobetasol ointment. The permeation results are shown in Table 13.

TABLE 13

Steady state flux of clobetasol propionate through human cadaver skin at 35° C.

| | Control J* (ng/cm$^2$/h) | Example 18 J* (ng/cm$^2$/h) |
|---|---|---|
| Cadaver skin | 17.2 ± 4.1 | 14.8 ± 1.0 |

*Skin flux measurements represent the mean and standard deviation of three determinations. Flux measurements reported are determined from the linear region of the cumulative amount versus time plots. The linear region are observed to be between 6–28 hours. If the experiment is continued, it is anticipated the steady state would continue.

As seen from Table 13, the formulation described in Example 18 has comparable steady state flux to the commercial ointment (Ratio 86%). This ratio is significantly higher than the ratio of formulation in Example 14, a polyvinyl alcohol based formulation, which has a ratio of 46%. This example demonstrates that formulations with protein based solidifying agents preserve flux of corticosteroids better than polyvinyl based formulations. The wear properties of formulation in Example 18 can be improved by the addition of plasticizers and fillers.

Example 19

To demonstrate the ability of the solidified solidifying formulations to reduce the transepidermal water loss (TEWL) the following experiment was conducted.

Placebo PVA formulation similar to the formulation described in Example 15 was applied to the top of the hand and the TEWL was measured on a site immediately adjacent to the solidified layer and on top of the solidified peel. The TEWL measurement of the site covered by the solidified layer was 33% lower than the untreated skin site.

Placebo Plastoid B formulation similar to the formulation described in Example 7 was applied to the top of the hand and the TEWL was measured on a side immediately adjacent to the solidified layer and on top of the solidified peel. The TEWL measurement on the site covered by the solidified layer was 30% lower than the untreated skin site.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A formulation for treating dermatitis or psoriasis, comprising:
   a) triamcinolone acetonide;
   b) a solvent vehicle, comprising:
      i) a volatile solvent system including ethanol, and
      ii) a non-volatile solvent system including propylene glycol, wherein the non-volatile solvent system facilitates the delivery of the triamcinolone acetonide at therapeutically effective rates; and
   c) a solidifying agent;
   wherein the formulation has a viscosity suitable for application and adhesion to a skin surface prior to evaporation of the volatile solvent system, the formulation upon being applied to a skin surface as a layer forms a solidified layer after at least partial evaporation of the volatile solvent system, and the triamcinolone acetonide is dermally deliverable at the therapeutically effective rate after the volatile solvent system is evaporated.

2. A formulation as in claim 1, wherein the non-volatile solvent system is capable of facilitating delivery of the triamcinolone acetonide at therapeutically effective rates over a sustained period of time.

3. A formulation as in claim 1, wherein the solidified layer is capable of adhering to the palm skin of human hands.

4. A formulation as in claim 1, wherein the non-volatile solvent system acts as a plasticizer for the solidifying agent.

5. A formulation as in claim 1, wherein the formulation further comprises an additional agent added to increase adhesion of the formulation when applied to a body surface.

6. A formulation as in claim 5, wherein the additional agent includes at least one member selected from the group consisting of copolymers of methylvinyl ether and maleic anhydride, polyethylene glycol and polyvinyl pyrrolidone, gelatin, low molecular weight polyisobutylene rubber, copolymer of acrylsan alkyl/octylacrylamido, aliphatic resins, aromatic resins, and combinations thereof.

7. A formulation as in claim 1, wherein the weight percentage of the volatile solvent system in the formulation is at least 10%.

8. A formulation as in claim 1, wherein the weight percentage of the volatile solvent system in the formulation is at least 20%.

9. A formulation as in claim 1, wherein the weight ratio of the non-volatile solvent system to the solidifying agent is from about 0.5:1 to about 2:1.

10. A formulation as in claim 1, wherein the volatile solvent system further comprises water.

11. A formulation as in claim 1, wherein the solvent vehicle is substantially free of water.

12. A formulation as in claim 1, wherein the volatile solvent system further comprises isopropyl alcohol.

13. A formulation as in claim 1, wherein the solidifying agent is a protein based substance.

14. A formulation as in claim 1, wherein the solidifying agent is a protein based substance including at least one member selected from the group of bovine gelatin, fish gelatin, zein, wheat protein, gluten, casein, and a combination thereof.

15. A formulation as in claim 1, wherein the volatile solvent system further comprises at least one additional volatile solvent selected from the group consisting of isopropyl alcohol, water, dimethyl ether, diethyl ether, butane, propane, isobutene, 1,1-difluoroethane, 1,1,1,2-tetrafluorethane, 1,1,1,2,3,3,3-heptafluoropropane, 1,1,1,3,3,3-hexafluoropropane, ethyl acetate, acetone, and combinations thereof.

16. A formulation as in claim 1, wherein the volatile solvent system further includes at least one solvent more volatile than water, and includes at least one member selected from the group consisting of denatured alcohol, methanol, propanol, isobutene, pentane, hexane, cyclomethicone, methyl ethyl ketone, and combinations thereof.

17. The formulation as in claim 1, wherein the non-volatile solvent system further includes at least one solvent selected from the group consisting of glycerol, isostearic acid, oleyl alcohol, oleic acid, and combinations thereof.

18. A formulation as in claim 1, wherein the non-volatile solvent system further includes at least one member selected from the group consisting of glycerol, isostearic acid, oleic acid, oleyl alcohol, trolamine, tromethamine, triacetin, sorbitan monolaurate, sorbitan monooleate, sorbitan monopalmitate, and combinations thereof.

19. A formulation as in claim 1, wherein the non-volatile solvent system further includes at least one member selected from the group consisting of benzoic acid, dibutyl sebecate, diglycerides, dipropylene glycol, eugenol, fatty acids, isopropyl myristate, mineral oil, oleyl alcohol, vitamin E, triglycerides, sorbitan fatty acid surfactants, triethyl citrate, and combinations thereof.

20. A formulation as in claim 1, wherein the non-volatile solvent system further includes at least one member selected from the group consisting of 1,2,6-hexanetriol, alkyltriols, alkyldiols, tocopherol, p-propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, cocoglycerides, coriander oil, corn oil, corn syrup, cottonseed oil, cresol, diacetin, diacetylated monoglycerides, diethanolamine, diglycerides, ethylene glycol, eucalyptus oil, fat, fatty alcohols, flavors, liquid sugars, ginger extract, glycerin, high fructose corn syrup, hydrogenated castor oil, IP palmitate, lemon oil, lime oil, limonene, monoacetin, monoglycerides, nutmeg oil, octyldodecanol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG fatty acid esters, PEG-stearate, PEG-oleate, PEG laurate, PEG fatty acid diesters, PEG-dioleate, PEG-distearate, PEG-castor oil, glyceryl behenate, PEG glycerol fatty acid esters, PEG glyceryl laurate, PEG glyceryl stearate, PEG glyceryl oleate, lanolin, lauric diethanolamide, lauryl lactate, lauryl sulfate, medronic acid, multisterol extract, myristyl alcohol, neutral oil, PEG-octyl phenyl ether, PEG-alkyl ethers, PEG-cetyl ether, PEG-stearyl ether, PEG-sorbitan fatty acid esters, PEG-sorbitan diisostearate, PEG-sorbitan monostearate, propylene glycol fatty acid esters, propylene glycol stearate, caprylate/caprate, sodium pyrrolidone carboxylate, sorbitol, squalene, triglycerides, alkyl aryl polyether alcohols, polyoxyethylene derivatives of sorbitan-ethers, saturated polyglycolyzed C8-C10 glycerides, N-methylpyrrolidone, honey, polyoxyethylated glycerides, dimethyl sulfoxide, azone and related compounds, dimethylformamide, N-methyl formamaide, fatty acid esters, fatty alcohol ethers, alkyl-amides, N-methylpyrrolidone related compounds, ethyl oleate, polyglycerized fatty acids, glycerol monooleate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, limnanthes alba seed oil, cetearyl alcohol, PEG-50 shea butter, shea butter, aloe vera juice, phenyl trimethicone, hydrolyzed wheat protein, and combinations thereof.

21. A formulation as in claim 1, wherein the solidifying agent includes at least one member selected from the group consisting of polyvinyl alcohol, esters of polyvinylmethylether/maleic anhydride copolymer, neutral copolymers of butyl methacrylate and methyl methacrylate, dimethylaminoethyl methacrylate-butyl methacrylate-methyl methacrylate copolymers, ethyl acrylate-methyl methacrylate-trimethylammonioethyl methacrylate chloride copolymers, prolamine, pregelatinized starch, ethyl cellulose, fish gelatin, gelatin, acrylates/octylacrylamide copolymers, and combinations thereof.

22. A formulation as in claim 1, wherein the solidifying agent includes at least one member selected from the group consisting of ethyl cellulose, hydroxy ethyl cellulose, hydroxy methyl cellulose, hydroxy propyl cellulose, hydroxypropyl methyl cellulose, carboxymethyl cellulose, methyl cellulose, polyether amides, corn starch, pregelatinized corn starch, polyether amides, shellac, polyvinyl pyrrolidone, polyisobutylene rubber, polyvinyl acetate phthalate and combinations thereof.

23. A formulation as in claim 1, wherein the solidifying agent includes at least one member selected from the group consisting of ammonia methacrylate, carrageenan, cellulose acetate phthalate aqueous, carboxy polymethylene, cellulose acetate, cellulose polymers, divinyl benzene styrene, ethylene vinyl acetate, silicone, guar gum, guar rosin, gluten, casein, calcium caseinate, ammonium caseinate, sodium caseinate, potassium caseinate, methyl acrylate, microcrystalline wax, polyvinyl acetate, PVP ethyl cellulose, acrylate, PEG/PVP, xantham gum, trimethyl siloxysilicate, maleic acid/anhydride copolymers, polacrilin, poloxamer, polyethylene oxide, poly glactic acid/poly-1-lactic acid, turpene resin, locust bean gum, acrylic copolymers, polyurethane dispersions, dextrin, polyvinyl alcohol-polyethylene glycol co-polymers, methacrylic acid-ethyl acrylate copolymers, methacrylic acid and methacrylate based polymers and combinations thereof.

24. A formulation as in claim 1, wherein the formulation further includes at least one drug selected from the group consisting of betamethasone dipropionate, clobetasol propionate, halobetasol propionate, diflorasone diacetate, amcinonide, desoximethasone, fluocinonide, halcinonide, mometasone furoate, betamethasone valerate, fluticasone propionate, fluocinolone acetonide, flurandrenolide, desonide, hydrocortisone butyrate, hydrocortisone valerate, alclometasone dipropionate, flumethasone pivolate, hydrocortisone, hydrocortisone acetate, tacrolimus, picrolimus, tazarotene, isotretinoin, cyclosporin, anthralin, vitamin D3, cholecalciferol, calcitriol, calcipotriol, tacalcitol, calcipotriene, and combinations thereof.

25. A formulation as in claim 1, wherein the formulation includes multiple pharmaceutically active agents.

26. A formulation as in claim 1, wherein the solidifying agent includes a methacrylic polymer.

27. A formulation as in claim 1, wherein the solidifying agent includes a methacrylic acid-ethyl acrylate copolymer.

28. A formulation as in claim 1, wherein the solidifying agent includes a polyvinyl alcohol-polyethylene glycol copolymer.

29. A formulation as in claim 1, wherein the solidified layer is sufficiently flexible and adhesive to the skin such that when applied to the skin at a human joint, the solidified layer will remain substantially intact on the skin upon bending of the human joint.

30. A formulation as in claim 1, wherein the solidified layer is sufficiently flexible and adhesive to the skin such that when applied to the palm skin of a human hand, the solidified layer will remain substantially intact on the palm skin upon movement of the hand.

31. A formulation as in claim 1, wherein the formulation is formulated to deliver the triamcinolone acetonide at a therapeutically effective rate for at least 2 hours following the formation of the solidified layer.

32. A formulation as in claim 1, wherein the formulation is formulated to deliver the triamcinolone acetonide at a therapeutically effective rate for at least 4 hours following the formation of the solidified layer.

33. A formulation as in claim 1, wherein the formulation is formulated to deliver the triamcinolone acetonide at a therapeutically effective rate for at least 8 hours following the formation of the solidified layer.

34. A formulation as in claim 1, wherein the formulation is formulated to deliver the triamcinolone acetonide at a therapeutically effective rate for at least 12 hours following the formation of the solidified layer.

35. A formulation as in claim 1, wherein the solidifying agent is dispersed in the solvent vehicle.

36. A formulation as in claim 1, wherein the solidifying agent is solvated in the solvent vehicle.

37. A formulation as in claim 1, wherein the non-volatile solvent system causes human skin irritation and at least one non-volatile solvent of the non-volatile solvent system reduces the skin irritation.

38. A formulation as in claim 37, wherein the non-volatile solvent which reduces skin irritation includes at least one member selected from the group consisting of glycerin, the propylene glycol, honey, and combinations thereof.

39. A formulation as in claim 1, wherein the formulation is formulated such that the solidified layer is formed within 15 minutes of application to standard skin at ambient conditions.

40. A formulation as in claim 1, wherein the formulation is formulated such that the solidified layer is formed within 5 minutes of application to standard skin at ambient conditions.

41. A formulation as in claim 1, wherein the formulation has an initial viscosity prior to skin application from about 100 to about 3,000,000 centipoises.

42. A formulation as in claim 1, wherein the formulation has an initial viscosity prior to skin application from about 1,000 to about 1,000,000 centipoises.

43. A formulation as in claim 1, wherein the weight percentage of the volatile solvent system is from about 10 wt % to about 85 wt %.

44. A formulation as in claim 1, wherein the weight percentage of the volatile solvent system is from about 20 wt % to about 50 wt %.

45. A formulation as in claim 1, wherein the non-volatile solvent includes at least two non-volatile solvents, and wherein at least one of the non-volatile solvents is included to improve compatibility of the non-volatile solvent system with the solidifying agent.

46. A formulation as in claim 1, wherein the solidified layer is coherent, flexible, and continuous.

47. A formulation as in claim 1, wherein the solidified layer, upon formation, is a soft, coherent solid that is peelable from a skin surface as a single piece or as only a few large pieces relative to the application size.

48. A formulation as in claim 1, wherein the solidified layer is formulated to deliver the triamcinolone acetonide transdermally.

49. A formulation as in claim 1, wherein the volatile solvent system comprises a volatile solvent whose boiling point is below 20° C.

50. A formulation as in claim 49, wherein the volatile solvent with the boiling point below 20° C. is completely dissolved in the formulation.

51. A formulation as in claim 49, wherein the volatile solvent with the boiling point below 20° C. is included in the formulation as a propellant for pressurized spray-on application.

52. A formulation as in claim 49, wherein the volatile solvent with the boiling point below 20° C. is a hydrofluorocarbon.

53. A formulation as in claim 49, wherein the at least one solvent whose boiling point is below 20° C. includes at least one member selected from the group consisting of dimethyl ether, butane, 1,1-difluoroethane, 1,1,1,2-tetrafluorethane, 1,1,1,2,3,3,3-heptafluoropropane, 1,1,1,3,3,3-hexafluoropropane, and combinations thereof.

54. A formulation as in claim 1, wherein the weight ratio of the non-volatile solvent system to the solidifying agent is from about 0.2:1 to about 4:1.

55. A method of dermally delivering a drug for treating dermatitis or psoriasis, comprising:
a) applying an adhesive solidifying formulation to a skin surface of a subject suffering from dermatitis or psoriasis, the adhesive solidifying formulation comprising:
    i) triamcinolone acetonide,
    ii) a solvent vehicle, comprising:
        a volatile solvent system including ethanol, and
        a non-volatile solvent system including propylene glycol, wherein the non-volatile solvent system is capable of facilitating delivery of the triamcinolone acetonide at a therapeutically effective rate over a sustained period of time, and
    iii) a solidifying agent,
wherein the formulation has a viscosity suitable for application and adhesion to the skin surface prior to evaporation of the volatile solvent system;
b) solidifying the formulation to form a solidified layer on the skin surface by at least partial evaporation of the volatile solvent system; and
c) dermally delivering the triamcinolone acetonide from the solidified layer to the skin at a the therapeutically effective rate for treating the dermatitis or psoriasis over a sustained period of time.

56. A method as in claim 55, wherein the skin surface is the palm skin of the hand.

57. A method as in claim 55, wherein the step of applying includes applying the formulation at a thickness from about 0.01 mm to about 3 mm.

58. A method as in claim 55, wherein the step of applying includes applying the formulation at a thickness from about 0.05 mm to about 1 mm.

59. A method as in claim 55, wherein the non-volatile solvent system includes multiple non-volatile solvents admixed together.

60. A method as in claim 55, wherein the volatile solvent system further includes at least one member selected from the group consisting of isopropyl alcohol, water, dimethyl ether, diethyl ether, butane, propane, isobutene, 1,1-difluoroethane, 1,1,1,2-tetrafluorethane, 1,1,1,2,3,3,3-heptafluoropropane, 1,1,1,3,3,3-hexafluoropropane, ethyl acetate, acetone, and combinations thereof.

61. A method as in claim 55, wherein the volatile solvent system further includes at least one member selected from the group consisting of denatured alcohol, methanol, propanol, isobutene, pentane, hexane, cyclomethicone, methyl ethyl ketone, and combinations thereof.

62. A method as in claim 55, wherein the non-volatile solvent system further includes at least one member selected from the group consisting of glycerol, isostearic acid, oleic acid, oleyl alcohol, trolamine, tromethamine, triacetin, sorbitan monolaurate, sorbitan monooleate, sorbitan monopalmitate, and combinations thereof.

63. A method as in claim 55, wherein the non-volatile solvent system further includes at least one member selected from the group consisting of benzoic acid, dibutyl sebecate, diglycerides, dipropylene glycol, eugenol, fatty acids, isopropyl myristate, mineral oil, oleyl alcohol, vitamin E, triglycerides, sorbitan fatty acid surfactants, triethyl citrate, and combinations thereof.

64. A method as in claim 55, wherein the non-volatile solvent system further includes at least one member selected from the group consisting of 1,2,6-hexanetriol, alkyltriols, alkyldiols, tocopherol, p-propenylanisole, anise oil, apricot oil, dimethyl isosorbide, alkyl glucoside, benzyl alcohol, bees wax, benzyl benzoate, butylene glycol, caprylic/capric triglyceride, caramel, cassia oil, castor oil, cinnamaldehyde, cinnamon oil, clove oil, coconut oil, cocoa butter, cocoglycerides, coriander oil, corn oil, corn syrup, cottonseed oil, cresol, diacetin, diacetylated monoglycerides, diethanolamine, diglycerides, ethylene glycol, eucalyptus oil, fat, fatty alcohols, flavors, liquid sugars, ginger extract, glycerin, high fructose corn syrup, hydrogenated castor oil, IP palmitate, lemon oil, lime oil, limonene, monoacetin, monoglycerides, nutmeg oil, octyldodecanol, orange oil, palm oil, peanut oil, PEG vegetable oil, peppermint oil, petrolatum, phenol, pine needle oil, polypropylene glycol, sesame oil, spearmint oil, soybean oil, vegetable oil, vegetable shortening, wax, 2-(2-(octadecyloxy)ethoxy)ethanol, benzyl benzoate, butylated hydroxyanisole, candelilla wax, carnauba wax, ceteareth-20, cetyl alcohol, polyglyceryl, dipolyhydroxy stearate, PEG-7 hydrogenated castor oil, diethyl phthalate, diethyl sebacate, dimethicone, dimethyl phthalate, PEG fatty acid esters, PEG-stearate, PEG-oleate, PEG laurate, PEG fatty acid diesters, PEG-dioleate, PEG-distearate, PEG-castor oil, glyceryl behenate, PEG glycerol fatty acid esters, PEG glyceryl laurate, PEG glyceryl stearate, PEG glyceryl oleate, lanolin, lauric diethanolamide, lauryl lactate, lauryl sulfate, medronic acid, multisterol extract, myristyl alcohol, neutral oil, PEG-octyl phenyl ether, PEG-alkyl ethers, PEG-cetyl ether, PEG-stearyl ether, PEG-sorbitan fatty acid esters, PEG-sorbitan diisosterate, PEG-sorbitan monostearate, propylene glycol fatty acid esters, propylene glycol stearate, caprylate/caprate, sodium pyrrolidone carboxylate, sorbitol, squalene, triglycerides, alkyl aryl polyether alcohols, polyoxyethylene derivatives of sorbitan-ethers, saturated polyglycolyzed C8-C10 glycerides, N-methylpyrrolidone, honey, polyoxyethylated glycerides, dimethyl sulfoxide, azone and related compounds, dimethylformamide, N-methyl formamaide, fatty acid esters, fatty alcohol ethers, alkyl-amides, N-methylpyrrolidone related compounds, ethyl oleate, polyglycerized fatty acids, glycerol monooleate, glyceryl monomyristate, glycerol esters of fatty acids, silk amino acids, PPG-3 benzyl ether myristate, Di-PPG2 myreth 10-adipate, honeyquat, sodium pyroglutamic acid, abyssinica oil, dimethicone, macadamia nut oil, limnanthes alba seed oil, cetearyl alcohol, PEG-50 shea butter, shea butter, aloe vera juice, phenyl trimethicone, hydrolyzed wheat protein, and combinations thereof.

65. A method as in claim 55, wherein the solidifying agent includes at least one member selected from the group consisting of polyvinyl alcohol, esters of polyvinylmethylether/maleic anhydride copolymer, neutral copolymers of butyl methacrylate and methyl methacrylate, dimethylaminoethyl methacrylate-butyl methacrylate-methyl methacrylate copolymers, ethyl acrylate-methyl methacrylate-trimethylammonioethyl methacrylate chloride copolymers, prolamine, pregelatinized starch, ethyl cellulose, fish gelatin, gelatin, acrylates/octylacrylamide copolymers, and combinations thereof.

66. A method as in claim 55, wherein the solidifying agent includes at least one member selected from the group consisting of ethyl cellulose, hydroxy ethyl cellulose, hydroxy methyl cellulose, hydroxy propyl cellulose, hydroxypropyl methyl cellulose, carboxymethyl cellulose, methyl cellulose, polyether amides, corn starch, pregelatinized corn starch, polyether amides, shellac, polyvinyl pyrrolidone, polyisobutylene rubber, polyvinyl acetate phthalate, and combinations thereof.

67. A method as in claim 55, wherein the solidifying agent includes at least one member selected from the group consisting of ammonia methacrylate, carrageenan, cellulose acetate phthalate aqueous, carboxy polymethylene, cellulose acetate, cellulose polymers, divinyl benzene styrene, ethylene vinyl acetate, silicone, guar gum, guar rosin, gluten, casein, calcium caseinate, ammonium caseinate, sodium caseinate, potassium caseinate, methyl acrylate, microcrystalline wax, polyvinyl acetate, PVP ethyl cellulose, acrylate, PEG/PVP, xantham gum, trimethyl siloxysilicate, maleic acid/anhydride copolymers, polacrilin, poloxamer, polyethylene oxide, poly glactic acid/poly-1-lactic acid, turpene resin, locust bean gum, acrylic copolymers, polyurethane dispersions, dextrin, polyvinyl alcohol-polyethylene glycol co-polymers, methacrylic acid-ethyl acrylate copolymers, methacrylic acid and methacrylate based polymers, and combinations thereof.

68. A method as in claim 55, wherein the formulation further includes at least one drug selected from the group consisting of betamethasone dipropionate, clobetasol propionate, halobetasol propionate, diflorasone diacetate, amcinonide, desoximethasone, fluocinonide, halcinonide, mometasone furoate, betamethasone valerate, fluticasone propionate, fluocinolone acetonide, flurandrenolide, desonide, hydrocortisone butyrate, hydrocortisone valerate, alclometasone dipropionate, flumethasone pivolate, hydrocortisone, hydrocortisone acetate, tacrolimus, picrolimus, tazarotene, isotretinoin, cyclosporin, anthralin, vitamin D3, cholecalciferol, calcitriol, calcipotriol, tacalcitol, calcipotriene, and combinations thereof.

69. A method as in claim 55, wherein the formulation includes multiple pharmaceutically active agents.

70. A method as in claim 55, wherein the formulation is left on the skin surface for at least 2 hours.

71. A method as in claim 55, wherein the formulation is left on the skin surface for at least 8 hours.

72. A method as in claim 55, wherein the weight ratio of the non-volatile solvent system to the solidifying agent is from about 0.5:1 to about 2:1.

73. A method as in claim 55, wherein the solidified layer is formed within about 15 minutes of the application to the skin surface.

74. A method as in claim 55, wherein the formulation has viscosity from about 100 to about 3,000,000 centipoises.

75. A method as in claim 55, wherein the solidified layer is coherent, flexible, and continuous.

76. A method as in claim 55, wherein the solidified layer, upon formation, is a soft, coherent solid that is peelable from a skin surface as a single piece or as only a few large pieces relative to the application size.

77. A method as in claim 55, further comprising the step of peeling the solidified layer from the skin after the sustained period of time to remove the solidified layer.

78. A method as in claim 55, further comprising the step of washing the solidified layer form the skin using a solvent after the sustained period of time to remove the solidified layer.

79. A method as in claim 55, wherein the weight ratio of the non-volatile solvent system to the solidifying agent in the formulation is from about 0.2:1 to about 4:1.

80. A drug-containing solidified layer devoid of volatile solvents for treating dermatitis or psoriasis, comprising:
 a) triamcinolone acetonide,
 b) a non-volatile solvent system including propylene glycol, wherein the non-volatile solvent system is capable of facilitating the delivery of the triamcinolone acetonide at a therapeutically effective rate over a sustained period of time; and
 c) a solidifying agent, wherein the solidified layer is capable of adhering to a skin surface to which the layer is applied.

81. A solidified layer as in claim 80, wherein the formulation further includes at least one drug selected from the group consisting of betamethasone dipropionate, clobetasol propionate, halobetasol propionate, diflorasone diacetate, amcinonide, desoximethasone, fluocinonide, halcinonide, mometasone furoate, betamethasone valerate, fluticasone propionate, fluocinolone acetonide, flurandrenolide, desonide, hydrocortisone butyrate, hydrocortisone valerate, alclometasone dipropionate, flumethasone pivolate, hydrocortisone, hydrocortisone acetate, tacrolimus, picrolimus, tazarotene, isotretinoin, cyclosporin, anthralin, vitamin D3, cholecalciferol, calcitriol, calcipotriol, tacalcitol, calcipotriene, and combinations thereof.

82. A solidified layer as in claim 80, wherein the solidified layer is sufficiently adhesive and flexible to remain substantially intact on standard skin under standard testing condition for at least 2 hours.

83. A solidified layer as in claim 80, which is coherent, flexible, and continuous.

84. A solidified layer as in claim 80, which is a soft, coherent solid that is peelable from a skin surface as a single piece or as only a few large pieces relative to the application size.

85. A solidified layer as in claim 80, wherein the weight ratio of the non-volatile solvent system to the solidifying agent is from about 0.5:1 to about 2:1.

86. A solidified layer as in claim 80, wherein the non-volatile solvent system further comprises at least one solvent selected from the group consisting of glycerol, isostearic acid, oleic acid, oleyl alcohol, and combinations thereof.

87. A solidified layer as in claim 80, wherein the solidified layer can be stretched in at least one direction by 5% without separation from the skin surface.

88. A solidified layer as in claim 80, wherein the non-volatile solvent system acts as a plasticizer for the solidifying agent.

89. A solidified layer as in claim 80, wherein solidified layer is sufficiently adhesive and flexible to remain substantially intact on a skin surface adjacent to a joint or muscle group where regular skin stretching occurs.

90. A solidified layer as in claim 80, wherein the solidified layer can be removed by washing.

91. A solidified layer as in claim 80, wherein the solidified layer is flux-enabling for the triamcinolone acetonide.

92. A solidified layer as in claim 80, wherein the weight ratio of the non-volatile solvent system to the solidifying agent is from about 0.2:1 to about 4:1.

93. A formulation for treating dermatitis or psoriasis, comprising:
   a) a drug including at least one member selected from the group consisting of clobetasol propionate, clobetasol, and combinations thereof;
   b) a solvent vehicle, comprising:
      i) a volatile solvent system including at least one volatile solvent, and
      ii) a non-volatile solvent system comprises at least one solvent selected from the group consisting of propylene glycol, glycerol, and combinations thereof, and at least one solvent selected from the group consisting of isostearic acid, oleic acid, and combinations thereof;
   c) a solidifying agent selected from the group consisting of polyvinyl alcohol, fish gelatin, gluten, casein, zein, and combinations thereof;
   wherein the weight ratio of the non-volatile solvent system to the solidifying agent is from about 0.2:1 to about 4:1 and wherein the formulation has a viscosity suitable for application and adhesion to a skin surface prior to evaporation of the volatile solvent system, the formulation after being applied to a skin surface as a layer forms a solidified, coherent, flexible, and continuous layer after at least partial evaporation of the volatile solvent system, and the drug continues to be topically delivered at the therapeutically effective rate after the volatile solvent system is at least substantially all evaporated.

* * * * *